US009608399B2

(12) United States Patent
Chuang et al.

(10) Patent No.: US 9,608,399 B2
(45) Date of Patent: Mar. 28, 2017

(54) 193 NM LASER AND AN INSPECTION SYSTEM USING A 193 NM LASER

(71) Applicant: KLA-Tencor Corporation, Milpitas, CA (US)

(72) Inventors: Yung-Ho Chuang, Cupertino, CA (US); J. Joseph Armstrong, Fremont, CA (US); Justin Dianhuan Liou, Santa Clara, CA (US); Vladimir Dribinski, Livermore, CA (US); John Fielden, Los Altos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 320 days.

(21) Appl. No.: 14/210,355

(22) Filed: Mar. 13, 2014

(65) Prior Publication Data
US 2016/0056606 A1 Feb. 25, 2016

Related U.S. Application Data

(60) Provisional application No. 61/803,108, filed on Mar. 18, 2013.

(51) Int. Cl.
H01S 3/23 (2006.01)
G01N 21/47 (2006.01)
(Continued)

(52) U.S. Cl.
CPC ........... H01S 3/2308 (2013.01); G01N 21/47 (2013.01); G01N 21/8806 (2013.01);
(Continued)

(58) Field of Classification Search
None
See application file for complete search history.

(56) References Cited

U.S. PATENT DOCUMENTS 3,755,704 A 8/1973 Spindt et al.
4,178,561 A 12/1979 Hon et al.
(Continued)

FOREIGN PATENT DOCUMENTS

CN 1286818 A 3/2001
CN 101702490 5/2010
(Continued)

OTHER PUBLICATIONS

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.
(Continued)

Primary Examiner — Armando Rodriguez
(74) Attorney, Agent, or Firm — Bever, Hoffman & Harms, LLP

(57) ABSTRACT

An improved laser uses a pump laser with a wavelength near 1109 nm and a fundamental wavelength near 1171 nm to generate light at a wavelength between approximately 189 nm and approximately 200 nm, e.g. 193 nm. The laser mixes the 1109 nm pump wavelength with the $5^{th}$ harmonic of the 1171 nm fundamental, which is at a wavelength of approximately 234.2 nm. By proper selection of non-linear media, such mixing can be achieved by nearly non-critical phase matching. This mixing results in high conversion efficiency, good stability, and high reliability.

18 Claims, 12 Drawing Sheets

(51) Int. Cl.

| | | |
|---|---|---|
| *G01N 21/95* | (2006.01) | |
| *H01S 3/30* | (2006.01) | |
| *G02F 1/35* | (2006.01) | |
| *G01N 21/88* | (2006.01) | |
| *H01S 3/06* | (2006.01) | |
| *H01S 3/067* | (2006.01) | |
| *H01S 3/0941* | (2006.01) | |
| *H01S 3/16* | (2006.01) | |
| *H01S 3/00* | (2006.01) | |

(52) U.S. Cl.
CPC ......... *G01N 21/9501* (2013.01); *G02F 1/353* (2013.01); *H01S 3/0092* (2013.01); *H01S 3/0602* (2013.01); *H01S 3/06708* (2013.01); *H01S 3/302* (2013.01); *G02F 2001/354* (2013.01); *G02F 2001/3507* (2013.01); *H01S 3/0078* (2013.01); *H01S 3/06758* (2013.01); *H01S 3/09415* (2013.01); *H01S 3/1618* (2013.01); *H01S 3/2375* (2013.01)

(56) References Cited

U.S. PATENT DOCUMENTS

| | | |
|---|---|---|
| 4,467,189 A | 8/1984 | Tsuchiya |
| 4,644,221 A | 2/1987 | Gutierrez et al. |
| 4,853,595 A | 8/1989 | Alfano et al. |
| 5,120,949 A | 6/1992 | Tomasetti |
| 5,144,630 A | 9/1992 | Lin |
| 5,563,702 A | 10/1996 | Emery et al. |
| 5,572,598 A | 11/1996 | Wihl et al. |
| 5,742,626 A | 4/1998 | Mead et al. |
| 5,760,809 A | 6/1998 | Malhotra et al. |
| 5,760,899 A | 6/1998 | Eismann |
| 5,825,562 A | 10/1998 | Lai et al. |
| 5,999,310 A | 12/1999 | Shafer et al. |
| 6,064,759 A | 5/2000 | Buckley et al. |
| 6,201,257 B1 | 3/2001 | Stettner et al. |
| 6,201,601 B1 | 3/2001 | Vaez-Iravani et al. |
| 6,212,310 B1 | 4/2001 | Waarts et al. |
| 6,220,914 B1 | 4/2001 | Lee et al. |
| 6,249,371 B1 | 6/2001 | Masuda et al. |
| 6,271,916 B1 | 8/2001 | Marxer et al. |
| 6,285,018 B1 | 9/2001 | Aebi et al. |
| 6,373,869 B1 | 4/2002 | Jacob |
| 6,498,801 B1 | 12/2002 | Dudelzak et al. |
| 6,590,698 B1 | 7/2003 | Ohtsuki et al. |
| 6,608,676 B1 | 8/2003 | Zhao et al. |
| 6,816,520 B1 | 11/2004 | Tulloch et al. |
| 6,859,335 B1 | 2/2005 | Lai et al. |
| 6,888,855 B1 | 5/2005 | Kopf |
| 7,098,992 B2 | 8/2006 | Ohtsuki et al. |
| 7,136,402 B1 | 11/2006 | Ohtsuki |
| 7,313,155 B1 | 12/2007 | Mu |
| 7,339,961 B2 | 3/2008 | Tokuhisa et al. |
| 7,352,457 B2 | 4/2008 | Kvamme et al. |
| 7,471,705 B2 | 12/2008 | Gerstenberger et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,593,437 B2 | 9/2009 | Staroudoumov et al. |
| 7,593,440 B2 | 9/2009 | Spinelli et al. |
| 7,609,309 B2 | 10/2009 | Brown et al. |
| 7,623,557 B2 | 11/2009 | Tokuhisa et al. |
| 7,627,007 B1 | 12/2009 | Armstrong et al. |
| 7,643,529 B2 | 1/2010 | Brown et al. |
| 7,715,459 B2 | 5/2010 | Brown et al. |
| 7,813,406 B1 | 10/2010 | Nguyen et al. |
| 7,822,092 B2 | 10/2010 | Ershov et al. |
| 7,875,948 B2 | 1/2011 | Hynecek et al. |
| 7,920,616 B2 | 4/2011 | Brown et al. |
| 7,952,633 B2 | 5/2011 | Brown et al. |
| 7,999,342 B2 | 8/2011 | Hsu et al. |
| 8,208,505 B2 | 6/2012 | Dantus et al. |
| 8,238,647 B2 | 8/2012 | Ben-Yishay et al. |
| 8,298,335 B2 | 10/2012 | Armstrong |
| 8,309,443 B2 | 11/2012 | Tanaka et al. |
| 8,391,660 B2 | 3/2013 | Islam |
| 8,503,068 B2 | 8/2013 | Sakuma |
| 8,514,587 B2 | 8/2013 | Zhang et al. |
| 8,629,384 B1 | 1/2014 | Biellak et al. |
| 8,686,331 B2 | 4/2014 | Armstrong |
| 8,755,417 B1 * | 6/2014 | Dribinski .............. G02F 1/3532 372/21 |
| 8,873,596 B2 | 10/2014 | Dribinski |
| 8,891,079 B2 | 11/2014 | Zhao et al. |
| 8,929,406 B2 | 1/2015 | Chuang et al. |
| 2001/0000977 A1 | 5/2001 | Vaez-Iravani et al. |
| 2002/0109110 A1 | 8/2002 | Some et al. |
| 2002/0191834 A1 | 12/2002 | Fishbaine |
| 2003/0043876 A1 | 3/2003 | Lublin et al. |
| 2003/0147128 A1 | 8/2003 | Shafer et al. |
| 2003/0161374 A1 | 8/2003 | Lokai |
| 2004/0080741 A1 | 4/2004 | Marxer et al. |
| 2005/0041702 A1 | 2/2005 | Fermann et al. |
| 2005/0110988 A1 | 5/2005 | Nishiyama et al. |
| 2005/0111081 A1 | 5/2005 | Shafer et al. |
| 2005/0122021 A1 | 6/2005 | Smith et al. |
| 2005/0128473 A1 | 6/2005 | Karpol et al. |
| 2005/0157382 A1 | 7/2005 | Kafka et al. |
| 2005/0190452 A1 | 9/2005 | Govorkov et al. |
| 2005/0254049 A1 | 11/2005 | Zhao |
| 2005/0254065 A1 | 11/2005 | Stokowski |
| 2006/0028984 A1 | 2/2006 | Vaez-Iravani et al. |
| 2006/0171656 A1 | 8/2006 | Adachi et al. |
| 2006/0239535 A1 | 10/2006 | Takada |
| 2006/0291862 A1 | 12/2006 | Kawai |
| 2007/0002465 A1 | 1/2007 | Chuang et al. |
| 2007/0096648 A1 | 5/2007 | Nakajima et al. |
| 2007/0103769 A1 | 5/2007 | Kuwabara |
| 2007/0146693 A1 | 6/2007 | Brown et al. |
| 2007/0188744 A1 | 8/2007 | Leslie et al. |
| 2007/0211773 A1 | 9/2007 | Gerstenberger et al. |
| 2007/0263680 A1 | 11/2007 | Staroudoumov et al. |
| 2007/0291810 A1 | 12/2007 | Luo et al. |
| 2008/0182092 A1 | 7/2008 | Bondokov et al. |
| 2008/0186476 A1 | 8/2008 | Kusunose |
| 2008/0204737 A1 | 8/2008 | Ogawa |
| 2009/0084989 A1 | 4/2009 | Imai |
| 2009/0108207 A1 | 4/2009 | Liu |
| 2009/0128912 A1 | 5/2009 | Okada |
| 2009/0180176 A1 | 7/2009 | Armstrong et al. |
| 2009/0185583 A1 | 7/2009 | Kuksenkov et al. |
| 2009/0185588 A1 | 7/2009 | Munroe |
| 2009/0201952 A1 | 8/2009 | Luo et al. |
| 2009/0296755 A1 | 12/2009 | Brown et al. |
| 2010/0103409 A1 | 4/2010 | Ohshima et al. |
| 2010/0188655 A1 | 7/2010 | Brown et al. |
| 2010/0301437 A1 | 12/2010 | Brown |
| 2011/0073982 A1 | 3/2011 | Armstrong et al. |
| 2011/0085149 A1 | 4/2011 | Nathan |
| 2011/0101219 A1 | 5/2011 | Uchiyama et al. |
| 2011/0134944 A1 | 6/2011 | Kaneda et al. |
| 2011/0222565 A1 | 9/2011 | Horain et al. |
| 2011/0228263 A1 | 9/2011 | Chuang et al. |
| 2011/0279819 A1 | 11/2011 | Chuang et al. |
| 2012/0033291 A1 | 2/2012 | Kneip |
| 2012/0092657 A1 | 4/2012 | Shibata |
| 2012/0113995 A1 | 5/2012 | Armstrong |
| 2012/0120481 A1 | 5/2012 | Armstrong |
| 2012/0137909 A1 | 6/2012 | Hawes et al. |
| 2012/0160993 A1 | 6/2012 | Nevet et al. |
| 2012/0314286 A1 | 12/2012 | Chuang et al. |
| 2013/0009069 A1 | 1/2013 | Okada |
| 2013/0016346 A1 | 1/2013 | Romanovsky et al. |
| 2013/0020491 A1 | 1/2013 | Mazzillo |
| 2013/0021602 A1 | 1/2013 | Dribinski et al. |
| 2013/0064259 A1 | 3/2013 | Wakabayashi et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0169957 A1 | 7/2013 | Wolf et al. |
| 2013/0176552 A1 | 7/2013 | Brown et al. |

(56) References Cited

U.S. PATENT DOCUMENTS

| | | | |
|---|---|---|---|
| 2013/0194445 A1 | 8/2013 | Brown et al. | |
| 2013/0264481 A1 | 10/2013 | Chern et al. | |
| 2013/0313440 A1* | 11/2013 | Chuang | G01N 21/8806 250/372 |
| 2013/0336574 A1 | 12/2013 | Nasser-Ghodsi et al. | |
| 2014/0034816 A1 | 2/2014 | Chuang et al. | |
| 2014/0071520 A1 | 3/2014 | Armstrong | |
| 2014/0111799 A1 | 4/2014 | Lei et al. | |
| 2014/0153596 A1 | 6/2014 | Chuang et al. | |
| 2014/0158864 A1 | 6/2014 | Brown et al. | |
| 2014/0204963 A1 | 7/2014 | Chuang et al. | |
| 2014/0226140 A1 | 8/2014 | Chuang et al. | |
| 2014/0291493 A1 | 10/2014 | Chuang et al. | |
| 2014/0305367 A1 | 10/2014 | Chuang et al. | |
| 2015/0007765 A1 | 1/2015 | Dribinski | |
| 2015/0177159 A1 | 6/2015 | Brown et al. | |
| 2015/0200216 A1 | 7/2015 | Muramatsu et al. | |
| 2015/0275393 A1 | 10/2015 | Bondokov et al. | |
| 2015/0294998 A1 | 10/2015 | Nihtianov | |

FOREIGN PATENT DOCUMENTS

| | | |
|---|---|---|
| DE | 102007004235 | 1/2008 |
| EP | 0532927 | 3/1993 |
| EP | 0746871 B1 | 5/2000 |
| EP | 0602983 B1 | 6/2000 |
| EP | 1194804 B1 | 7/2003 |
| EP | 1939917 A2 | 7/2008 |
| EP | 2013951 | 1/2009 |
| JP | H0511287 A | 1/1993 |
| JP | 2002-258339 A | 9/2002 |
| JP | 2003043533 A | 2/2003 |
| JP | 2006-60162 A | 3/2006 |
| JP | 2007086108 A | 4/2007 |
| JP | 2007-206452 A | 8/2007 |
| JP | 2007249092 A | 9/2007 |
| JP | 2007298932 A | 11/2007 |
| JP | 2009-145791 | 7/2009 |
| JP | 2010003755 A | 1/2010 |
| JP | 2010-54547 | 3/2010 |
| JP | 2010-256784 | 11/2010 |
| JP | 2011-23532 A | 2/2011 |
| JP | 2011-128330 A | 6/2011 |
| WO | 9532518 A1 | 11/1995 |
| WO | 9617372 A1 | 6/1996 |
| WO | 03/069263 | 8/2003 |
| WO | 2009/082460 | 7/2009 |
| WO | 2010/037106 | 4/2010 |
| WO | 2012/154468 | 11/2012 |
| WO | 2013/015940 A2 | 1/2013 |
| WO | 2013006867 A1 | 1/2013 |
| WO | 2014067754 A2 | 5/2014 |

OTHER PUBLICATIONS

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.

Dianov et al. "Bi-doped fiber lasers: new type of high-power radiaton sources", Conference on Lasers and Electro-Optics, May 6-11, 2007, 2 pages.

Kalita et al. "Multi-watts narrow-linewidth all fiber Yb-doped laser operating at 1179 nm", Optics Express, 18 (6), pp. 5920-5925 (2010).

Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).

Mead et al. "Solid-state lasers for 193-nm photolithography", Proc. SPIE 3051, Optical Microlithography X, pp. 882-889 (Jul. 7, 1997).

Saikawa et al. "52 mJ narrow-bandwidth degenerated optical parametric system with a large-aperture periodically poled MgO:LiNbO3 device", Optics Letters, 31 (#21), 3149-3151 (2006).

Sakuma et al. "High power, narrowband, DUV laser source by frequency mixing in CLBO", Advanced High-Power Lasers and Applications, Nov. 2000, pp. 7-14, Ushio Inc.

Sakuma et al. "True CW 193.4-nm light generation based on frequency conversion of fiber amplifiers", Optics Express 19 (#16), 15020-15025 (2011).

Sasaki et al. "Progress in the growth of a CsLiB6O10 crystal and its application to ultraviolet light generation", Optical Materials, vol. 23, 343-351 (2003).

Shirakawa et al. "High-power Yb-doped photonic bandgap fiber amplifier at 1150-1200nm", Optics Express 17 (2), 447-454 (2009).

Ter-Mikirtychev et al. "Tunable LiF:F2-color center laser with an intracavity integrated-optic output coupler", Journal of Lightwave Technology, 14 (10), 2353-2355 (1996).

Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.

Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.

File history for U.S. Appl. No. 11/735,967, filed Apr. 16, 2007 by Vladimir L. Dribinski et al.

Fu, Xiaoqian, "Higher Quantum Efficiency by Optimizing GaN Photocathode Structure", 978-1-4244-6644-3/10/ ® 2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Utsumi, Vacuum Microelectrnoics: What's New and Exciting, IEEE vol. 38, No. 10, Oct. 1991, 8 pgs.

Armstrong, Carter M., The Quest for the Ultimate Vacuum Tube, Spectrum IEEE, Dec. 2015, 4 pgs.

Serbun, Pavel et al., Stable field emission of single B-doped . . . , JVSTB, 31, 02B101 (2013); doi: 10.1116/1.4765088, 7 pgs.

Sato, T. et al., Fabrication and characterization of HfC coated . . . , J. Vac. Sci. Technol. B 2194), published Jul. 31, 2003, 5 pgs.

Nagao, Masayoshi, Fabrication of a Field Emitter Array with a Built-In Einzel Lens, JJAP 48 (2008) 06FK02, 4 pgs.

Rakhshandehroo, M.R., et al., Fabrication of a self-aligned silicon field emission . . . , JVSTB, 16, 765 (1998); doi: 10.1116/1,589900, 6 pgs.

Rakhshandehroo, M.R., et al., Field emission from gated Si emitter tips with precise . . . , JVSTB, 15, 2777 (1997); doi: 10.1116/1.589726, 6 pgs.

Ding, Meng, Field Emission from Silicon, MIT 2001, 277 pgs.

Koike, Akifuni, Field Emitter Equipped With a Suppressor to Control Emission Angel, IEEE Electron Device Letters, vol. 34, No. 5, May 2013, 3 pgs.

(56) References Cited

OTHER PUBLICATIONS

Nagao, Masayoshi, Cathode Technologies for Field Emission Displays, IEJ Trans 2006; 1:171-178, 8 pgs.
Neo, Yoichiro, Electron Optical Properties of Microcolumn with Field Emitter, JJAP 52 (2013) 036603, 5 pgs.
Fowler, R.H. et al., Electron Emission in Intense Electric Fields, Mar. 31, 1928, 9 pgs.
Fanton, J. T., et al., "Multiparameter Measurements of Thin Films Using beam-profile reflectometry", Journal of Applied Physics, vol. 73, No. 11, p. 7035 (1993).
International Search Report and Written Opinion dated Jul. 11, 2014 for PCT/US2014/030989, filed Mar. 18, 2014 in the name of KLA-Tencor Corporation.
International Search Report and Written Opinion dated May 20, 2014 for PCT/US2014/016198, filed Feb. 13, 2014 in the name of KLA-Tencor Corporation.
KLA-Tencor Corporation, filed U.S. Appl. No. 14/248,045, filed Apr. 8, 2014 and entitled "Passivation of Nonlinear Optical Crystals".
KLA-Tencor Corporation, filed U.S. Appl. No. 62/059,368, filed Oct. 3, 2014 and entitled "183nm Laser and Inspection System".
Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.
KLA-Tencor Corporation; PCT International Search Report dated Dec. 29, 2015 for Application No. PCT/US2015/051538, 3 pages.

\* cited by examiner

US 9,608,399 B2

193 NM LASER AND AN INSPECTION SYSTEM USING A 193 NM LASER

PRIORITY APPLICATION

The present application claims priority to U.S. Provisional Application 61/803,108, entitled "193 nm laser and an inspection system using a 193 nm laser" and filed on Mar. 18, 2013, which is incorporated by reference herein.

RELATED APPLICATIONS

The present application is related to U.S. patent application Ser. No. 11/735,967, entitled "Coherent light generation below about 200 nm" and filed Apr. 16, 2007, U.S. patent application Ser. No. 13/558,318, entitled "Solid-State Laser And Inspection System Using 193 nm Laser" and filed Jul. 25, 2012, and U.S. Provisional Application 61/764,441, entitled "193 nm Laser and an Inspection System Using a 193 nm Laser", and filed Feb. 13, 2013, and U.S. patent application Ser. No. 14/170,384, entitled "193 nm Laser and Inspection System" and filed Jan. 31, 2014, all of which are incorporated by reference herein.

BACKGROUND OF THE DISCLOSURE

Field of the Disclosure

The present application relates to a fiber-optic-based laser that generates light between about 189 nm and about 200 nm in wavelength, such as light at a wavelength near 193 nm, and is suitable for use in photomask, reticle, or wafer inspection.

Related Art

The integrated circuit industry requires inspection tools with increasingly higher resolution to resolve ever smaller features of integrated circuits, photomasks, solar cells, charge coupled devices etc., as well as detect defects whose sizes are of the order of, or smaller than, feature sizes. Short wavelength light sources, e.g. sources generating light under 200 nm, can provide such resolution. However, the light sources capable of providing such short wavelength light are substantially limited to excimer lasers and a small number of solid-state and fiber lasers. Unfortunately, each of these lasers has significant disadvantages.

An excimer laser generates an ultraviolet light, which is commonly used in the production of integrated circuits. An excimer laser typically uses a combination of a noble gas and a reactive gas under high pressure conditions to generate the ultraviolet light. A conventional excimer laser generating 193.4 nm wavelength light, which is increasingly a highly desirable wavelength in the integrated circuit industry, uses argon (as the noble gas) and fluorine (as the reactive gas). Unfortunately, fluorine is toxic and corrosive, thereby resulting in high cost of ownership. Moreover, such lasers are not well suited to inspection applications because of their low repetition rate (typically from about 100 Hz to several kHz) and very high peak power that would result in damage of samples during inspection.

A small number of solid-state and fiber-based lasers producing sub-200 nm output are known in the art. Unfortunately, most of these lasers have very low power output (e.g. under 60 mW), or very complex design, such as two different fundamental sources or eighth harmonic generation, both of which are complex, unstable, expensive and/or commercially unattractive.

Therefore, a need arises for a laser capable of generating 193 nm light, yet overcoming the above disadvantages.

SUMMARY OF THE DISCLOSURE

A laser for generating ultraviolet light with a vacuum wavelength of between approximately 189 nm and approximately 200 nm, e.g. approximately 193 nm, is described. This laser includes a pump laser, a fundamental laser, and a frequency mixing stage. The fundamental laser can generate a fundamental frequency corresponding to a wavelength of between approximately 1150 nm and approximately 1175 nm, e.g. approximately 1171 nm. Where a wavelength value without qualification is given in this specification, it is to be assumed that wavelength value refers to the wavelength in vacuum. The fundamental frequency can be generated by Raman shifting a pump laser at a frequency corresponding to a wavelength of approximately 1109 nm.

A first stage can combine portions of the fundamental frequency to generate a second harmonic frequency. In one embodiment, a second stage can combine portions of the second harmonic frequency to generate a fourth harmonic frequency. A third stage can combine a portion of the fundamental frequency and the fourth harmonic frequency to generate a fifth harmonic frequency. A fourth stage can combine a portion of the pump frequency and the fifth harmonic frequency to generate a sum frequency corresponding to a wavelength of approximately 193.4 nm. The first stage can include a Lithium triborate (LBO) crystal, whereas each of the second, third, and fourth stages may include a Cesium Lithium Borate (CLBO) crystal. In one embodiment, one or more of the second, third, and fourth stages includes an annealed non-linear crystal such as a CLBO crystal.

In another embodiment, a second stage can combine the fundamental frequency and the second harmonic frequency to generate a third harmonic frequency. A third stage can combine the second harmonic frequency and the third harmonic frequency to generate a fifth harmonic frequency. A fourth stage can combine a portion of the pump frequency and the fifth harmonic frequency to generate a sum frequency of approximately 193.4 nm. The first and second stages can include a LBO crystal, the third stage can include beta-Barium Borate (BBO) crystal, and the fourth stage can include a CLBO crystal. In one embodiment, one or more of the second, third, and fourth stages can include an annealed LBO, BBO, and/or CLBO crystal.

In some embodiments, the laser can also include an optical amplifier for amplifying the fundamental frequency. This optical amplifier can include a doped photonic band-gap fiber optical amplifier, a germania-doped Raman amplifier, or an undoped silica fiber Raman amplifier. The seed laser can include a Raman fiber laser, a low-power, ytterbium (Yb)-doped fiber laser, a photonic band-gap fiber laser, or an infra-red diode laser such as a diode laser using quantum dot technology.

The laser can also include beam splitters and/or prisms for providing the fundamental frequency to the first, second or third stages as appropriate. At least one mirror or prism can be used for directing the fundamental frequency to an appropriate stage. In one embodiment, a set of mirrors or prisms can be used for directing unconsumed harmonics to appropriate stages.

In some embodiments, all of the pump laser output is directed to the fundamental laser. At the output of the fundamental laser, unconsumed pump laser light is separated from the fundamental laser light and is directed to the frequency mixing stage. In another embodiment, a small portion of the pump laser output is directed to the frequency mixing stage, while most of the pump laser output is directed to the fundamental laser.

In some embodiments, the fourth stage may comprise an optical cavity to recirculate the pump frequency so as to maintain a high power density of the pump frequency within the non-linear crystal to improve the efficiency of the fourth stage.

In one embodiment, the second stage comprises an optical cavity that recirculates the fundamental to maintain a high power density of the fundamental within the non-linear crystal to improve the efficiency of the second stage. In another embodiment, the third stage comprises an optical cavity that recirculates the fundamental so as to maintain a high power density of the fundamental within the non-linear crystal to improve the efficiency of the third stage.

A method of generating light at between approximately 189 nm and approximately 200 nm wavelength, e.g. approximately 193 nm wavelength light, is also described. This method includes generating a fundamental frequency corresponding to a wavelength of approximately 1171 nm from a pump frequency corresponding to a wavelength of approximately 1109 nm. Portions of the fundamental frequency can be combined to generate a second harmonic frequency. Portions of the second harmonic frequency can be combined to generate a fourth harmonic frequency. The fundamental frequency and the fourth harmonic frequency can be combined to generate a fifth harmonic frequency. The pump frequency and the fifth harmonic frequency can be combined to generate a sum frequency corresponding to a wavelength of approximately 193.4 nm. In some embodiments of this method, the pump frequency is recirculated in the cavity that mixes it with the fifth harmonic in order to more efficiently convert the fifth harmonic to the output wavelength. In some embodiments of this method, the fundamental is recirculated in the cavity that mixes it with the fourth harmonic in order to more efficiently convert the fourth harmonic to the fifth harmonic.

Another method of generating light is also described. This method includes generating a fundamental frequency of approximately 1171 nm from a pump frequency corresponding to wavelength of approximately 1109 nm. Portions of the fundamental frequency can be combined to generate a second harmonic frequency. Portions of the second harmonic frequency can be combined with the fundamental frequency to generate a third harmonic frequency. The second harmonic frequency and the third harmonic frequency can be combined to generate a fifth harmonic frequency. The pump frequency and the fifth harmonic frequency can be combined to generate a sum frequency corresponding to a wavelength of between approximately 189 nm and approximately 200 nm, e.g. approximately 193.4 nm. In some embodiments of this method, the pump frequency is recirculated in the cavity that mixes it with the fifth harmonic in order to more efficiently convert the fifth harmonic to the output wavelength. In some embodiments of this method, the fundamental is recirculated in the cavity that mixes it with the second harmonic in order to more efficiently convert the second harmonic to the third harmonic.

Various systems for inspecting samples are described. These systems can include a laser for generating an output beam of radiation at a wavelength between approximately 189 nm and approximately 200 nm, e.g. approximately 193 nm. The laser can include a pump laser for generating a pump frequency corresponding to a wavelength of approximately 1109 nm, a fundamental laser for generating a fundamental frequency corresponding to a wavelength of approximately 1171 nm, and a frequency mixing module for generating the output beam. The pump frequency, the fundamental frequency and the plurality of frequencies can be used to generate the approximately 193 nm radiation. In some embodiments, the laser is optimized to use at least one unconsumed frequency from one harmonic generator or frequency mixing module in another stage. In one embodiment, the pump frequency in recirculated in the final frequency mixing module. The systems can further include means for focusing the output beam on the sample and means for collecting scattered or reflected light from the sample.

An optical inspection system for inspecting a surface of a photomask, reticle, or semiconductor wafer for defects is described. This inspection system incorporates one of the lasers described herein for generating light at a wavelength of between approximately 189 nm and approximately 200 nm, e.g. approximately 193 nm. The laser can include a pump laser for generating a pump frequency corresponding to a wavelength of approximately 1109 nm, a fundamental laser for generating a fundamental frequency corresponding to a wavelength of approximately 1171 nm, and a frequency mixing module for generating a plurality of frequencies. The pump frequency, the fundamental frequency and the plurality of frequencies can be used to generate the approximately 193 nm radiation. In some embodiments, the laser is optimized to use at least one unconsumed frequency from one harmonic generator or frequency mixing module in another stage. In one embodiment, the pump frequency is recirculated in the final frequency mixing module. This inspection system simultaneously illuminates and detects two channels of signal or image. Both channels are simultaneously detected on the same sensor. The two channels may comprise reflected and transmitted intensity when the inspected object is transparent (for example a reticle or photomask), or may comprise two different illumination modes, such as angles of incidence, polarization states, wavelength ranges, or some combination thereof.

An optical inspection system for inspecting a surface of a photomask, reticle, or semiconductor wafer for defects is also described. This system can include a light source for emitting an incident light beam along an optical axis, the light source generating a wavelength of between approximately 189 nm and approximately 200 nm, e.g. approximately 193 nm, from a pump frequency corresponding to a wavelength of approximately 1109 nm and a fundamental frequency corresponding to a wavelength of approximately 1171 nm. An optical system disposed along the optical axis includes a plurality of optical components configured to direct the incident light beam onto a surface of the photomask, reticle, or semiconductor wafer. The system includes a transmitted light detector arrangement for sensing a light intensity of transmitted light. The system further includes a reflected light detector arrangement for sensing a light intensity of reflected light.

A surface inspection apparatus is also described. This apparatus can include a laser for generating a beam of radiation at a wavelength between approximately 189 nm and approximately 200 nm, e.g. approximately 193 nm. This laser can include generating the beam of radiation from a pump frequency corresponding to a wavelength of approximately 1109 nm, a fundamental frequency corresponding to a wavelength of approximately 1171 nm, and a plurality of harmonic generators and frequency mixing modules for generating a plurality of frequencies, wherein the pump frequency, the fundamental frequency and the plurality of frequencies are used to generate the approximately 193 nm radiation. In some embodiments, the laser is optimized to use at least one unconsumed frequency from one harmonic generator or frequency mixing module in another stage. In one embodiment, the pump frequency in recirculated in the final frequency mixing module. An illumination system of the apparatus can be configured to focus the beam of radiation at a non-normal incidence angle relative to a surface to form an illumination line on the surface substantially in a plane of incidence of the focused beam. The plane of incidence is defined by the focused beam and a direction that is through the focused beam and normal to the surface. A collection system of the apparatus can be configured to image the illumination line. In one embodiment, the collection system can include an imaging lens for collecting light scattered from a region of the surface comprising the illumination line. A focusing lens can be provided for focusing the collected light. A device including an array of light sensitive elements can also be provided. In this array, each light sensitive element of the array of light sensitive elements can be configured to detect a corresponding portion of a magnified image of the illumination line.

An optical system for detecting anomalies of a sample is also described. This optical system includes one of the herein described lasers for generating an inspection beam at a wavelength of between approximately 189 nm and approximately 200 nm, e.g. approximately 193 nm. The laser can include a pump laser for generating a pump frequency corresponding to a wavelength of approximately 1109 nm, a fundamental laser for generating a fundamental frequency corresponding to a wavelength of approximately 1171 nm, and a plurality of harmonic generators and frequency mixing modules for generating a plurality of frequencies. The pump frequency, the fundamental frequency and the plurality of frequencies are used to generate the approximately 193 nm radiation. The system can include first optics for directing a first beam along a first path onto a first spot on a surface of the sample. The system can further include second optics for directing a second beam along a second path onto a second spot on the surface of the sample. The first and second paths are at different angles of incidence to the surface of the sample. Collection optics can include a curved mirrored surface that receives scattered radiation from the spot on the sample surface and focuses the scattered radiation to a first detector. The first detector provides an output value in response to the radiation focused onto it by the curved mirrored surface. Collection optics can further include lenses that receive scattered radiation from the spot on the sample surface and focus the scattered radiation to a second detector. The second detector provides an output value in response to the radiation focused onto it by said lenses. An instrument can be provided that causes relative motion between the first and second beams and the sample so that the first and second spots are scanned across the surface of the sample.

Another optical system for detecting anomalies of a sample is described. This optical system includes one of the herein described lasers for generating first and second beams at a wavelength of between approximately 189 nm and approximately 200 nm, e.g. approximately 193 nm. The laser can include a pump laser for generating a pump frequency corresponding to a wavelength of approximately 1109 nm, a fundamental laser for generating a fundamental frequency corresponding to a wavelength of approximately 1171 nm, and a plurality of harmonic generators and frequency mixing modules for generating a plurality of frequencies. The pump frequency, the fundamental frequency and the plurality of frequencies can be used to generate the approximately 193 nm radiation. Optics in the optical system are configured to receive the plurality of channels of light and combine the plurality of channels of light energy into a spatially separated combined light beam and direct the spatially separated combined light beam toward the sample. A data acquisition subsystem in the optical system includes at least one detector configured to detect reflected light from the sample. The data acquisition subsystem can be configured to separate the reflected light into a plurality of received channels corresponding to the plurality of channels of light.

A catadioptric imaging system with dark-field illumination is also described. This system can include an ultraviolet (UV) light source for generating UV light. The UV light source includes one of the herein described lasers for generating light at a wavelength of between approximately 189 nm and approximately 200 nm, e.g. approximately 193 nm. The laser can include a pump laser for generating a pump frequency corresponding to a wavelength of approximately 1109 nm, a fundamental laser for generating a fundamental frequency corresponding to a wavelength of approximately 1171 nm, a fifth harmonic generator, and a frequency mixing module for generating the approximately 193 nm wavelength light. Adaptation optics are also provided to control the illumination beam size and profile on the surface being inspected. An objective can include a catadioptric objective, a focusing lens group, and a zooming tube lens section in operative relation to each other. A prism can be provided for directing the UV light along the optical axis at normal incidence to a surface of a sample and directing specular reflections from surface features of the sample as well as reflections from optical surfaces of the objective along an optical path to an imaging plane.

DETAILED DESCRIPTION OF THE DRAWINGS

An improved fiber-optic based laser for generating 193 nm light is described. This laser combines the fifth harmonic (5ω) of a fundamental wavelength (u near 1171 nm) with a pump wavelength (ω0 near 1109 nm) to generate the 193 nm light. By proper selection of non-linear media, such mixing can be achieved using nearly non-critical phase matching, as described below. This mixing results in high conversion efficiency, good stability, and high reliability.

Figure 1:
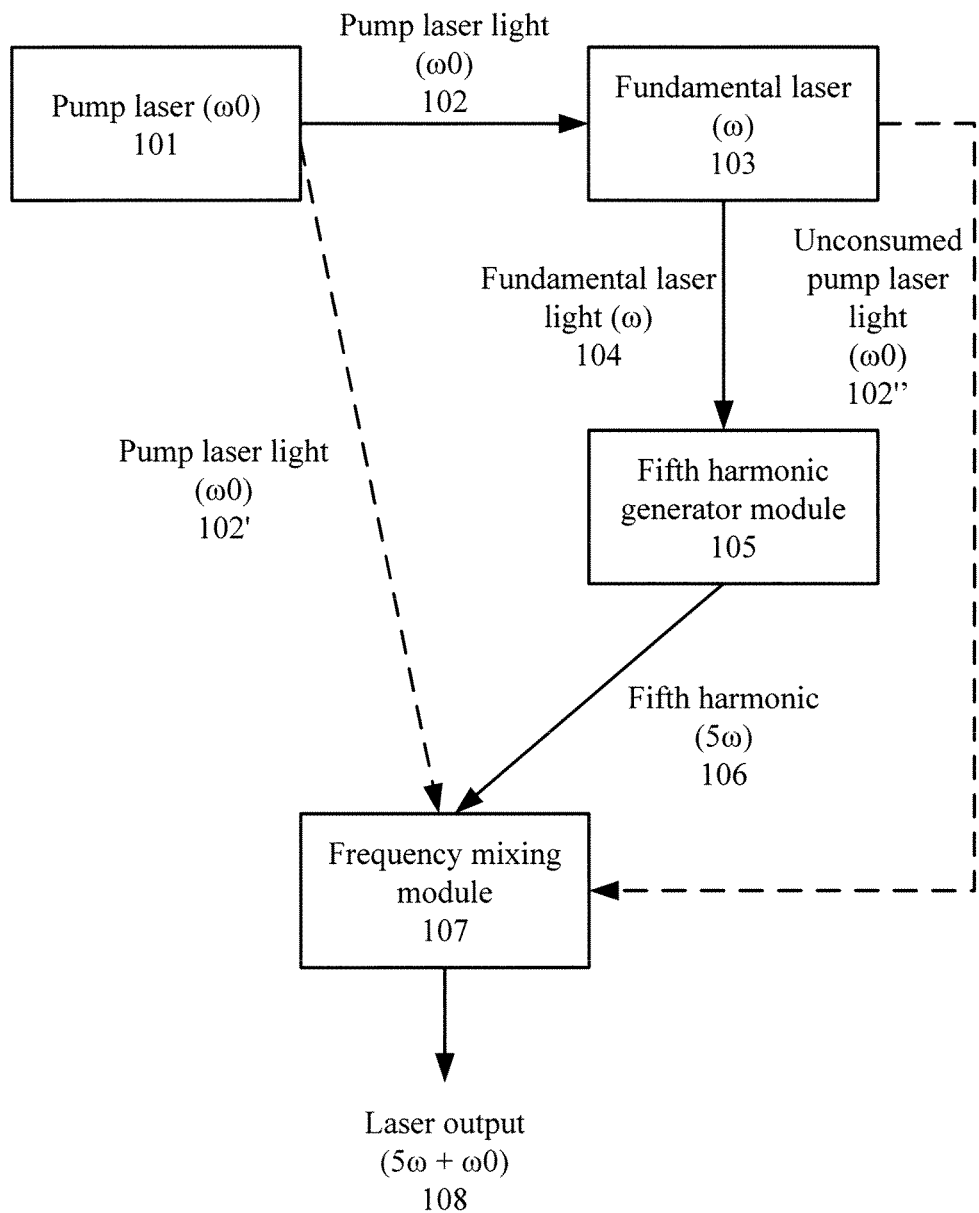
FIG. 1 illustrates a block diagram of an exemplary laser for generating 193 nm wavelength light using a fundamental wavelength ($\omega$) of approximately 1171 nm and a pump wavelength ($\omega 0$) of approximately 1109 nm.

FIG. 1 illustrates a simplified block diagram of an exemplary embodiment of a fiber-optic-based laser 100 for generating 193 nm light. In this embodiment, laser 100 includes a pump laser 101 operating at a wavelength near 1109 nm, which generates pump laser light 102 at a frequency corresponding to a wavelength of approximately 1109 nm, such as a wavelength of 1109.1 nm. For convenience, the pump wavelength will be designated herein by ω0. Pump laser 101 may comprise an Yb-doped fiber-optic laser or another laser. Pump laser 101 should preferably be stabilized and have a narrow bandwidth (such as a bandwidth containing 95% of the energy, i.e. E95 bandwidth, equal to about 300 pm or less). Wavelength selective devices such as fiber Bragg gratings, diffraction gratings or etalons, or distributed feedback can be used with pump laser 101 to control the wavelength and bandwidth. Pump laser light 102 at a frequency of ω0 is used to pump fundamental laser 103 which generates fundamental laser light 104 at a fundamental frequency designated herein by ω. Preferably the fundamental frequency ω corresponds to a wavelength of approximately 1171 nm, such as a wavelength of 1171.0 nm. Fundamental laser 103 can be implemented by a Raman fiber laser. Fundamental laser 103 should preferably be stabilized and have a narrow bandwidth. One exemplary embodiment of pump laser 101 and fundamental laser 103 is shown in more detail in FIG. 3 and described below.

The fundamental laser light 104 output by fundamental laser 103 is directed to a fifth harmonic generator module 105. Fifth harmonic generator module 105 includes multiple frequency conversion stages to generate the fifth harmonic (5ω) 106 of the fundamental. In preferred embodiments, the fifth harmonic 106 corresponds to a wavelength of approximately 234.2 nm. Exemplary embodiments of fifth harmonic generator module 105 are shown in FIGS. 2A and 2B and described below.

Figure 4:
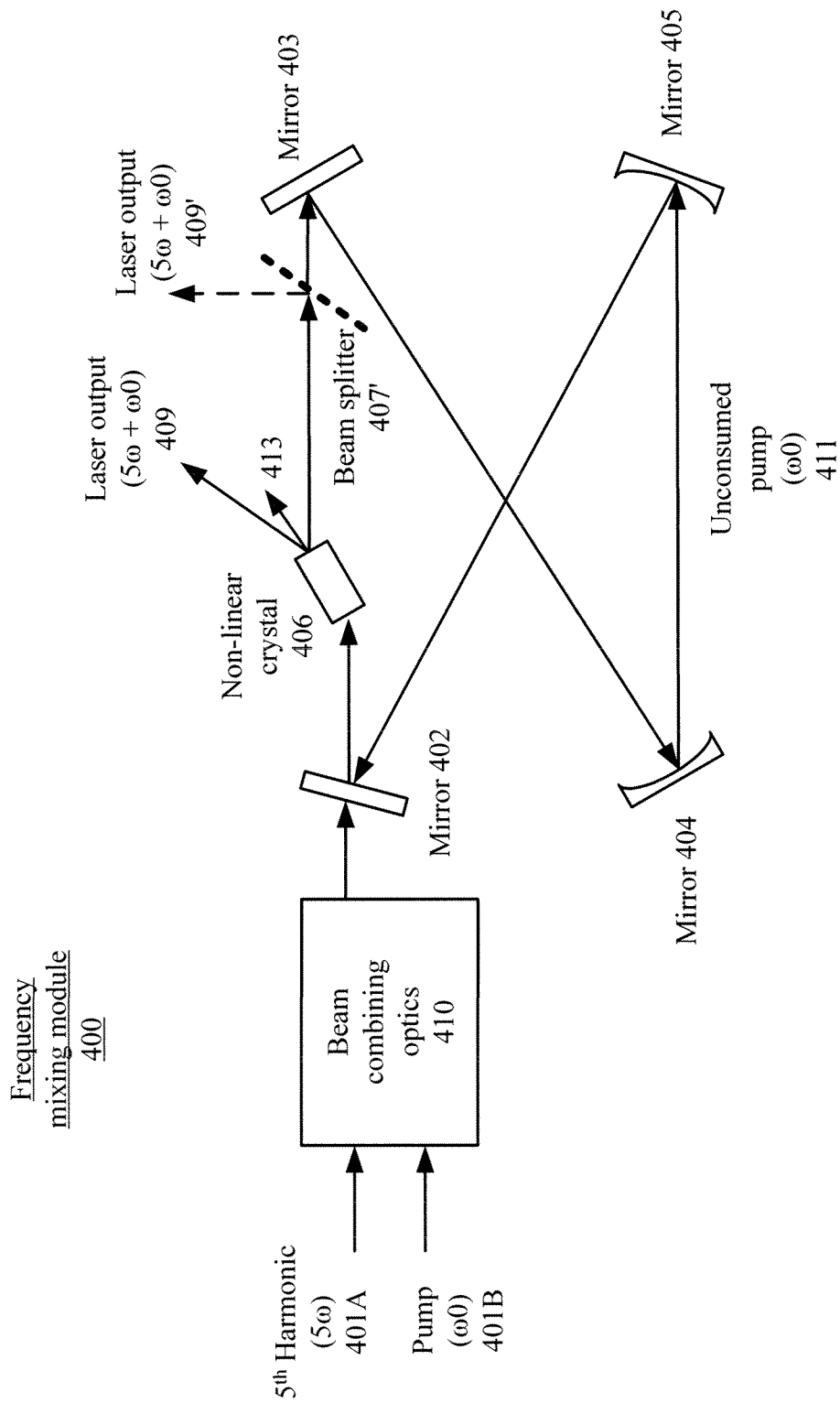
FIG. 4 illustrates a block diagram of an exemplary frequency mixing module.

A frequency mixing module 107 receives both the fifth harmonic 106 (from fifth harmonic generator 105) and pump laser light (ω0) to generate a laser output 108 at a wavelength of approximately 193.4 nm. Pump laser light (ω0) may be directed to frequency mixing module 107 by separating off a portion of the pump laser light 102' from the output of pump laser 101 or by directing unconsumed pump laser light 102" from fundamental laser 103. Frequency mixing module 107 comprises a non-linear crystal, preferably hydrogen-annealed CLBO (cesium lithium borate) or annealed CLBO. CLBO is nearly non-critically phase matched for wavelengths near 1109.1 nm and 234.2 nm for crystal temperatures below about 187° C. In preferred embodiments, the temperature of the CLBO is about 120° C., which results in a walk-off angle of about 7 mrad, thereby allowing the use of a long crystal (approximately 15 mm to 20 mm in some embodiments). More details of an exemplary embodiment of frequency mixing module 107 are shown in FIG. 4 and described below. More details about hydrogen-annealed non-linear crystals, including hydrogen-annealed CLBO, can be found in U.S. patent application Ser. No. 13/488,635, entitled "Hydrogen Passivation Of Non-Linear Optical Crystals", filed on Jun. 1, 2012, and incorporated by reference herein.

Figure 2A:
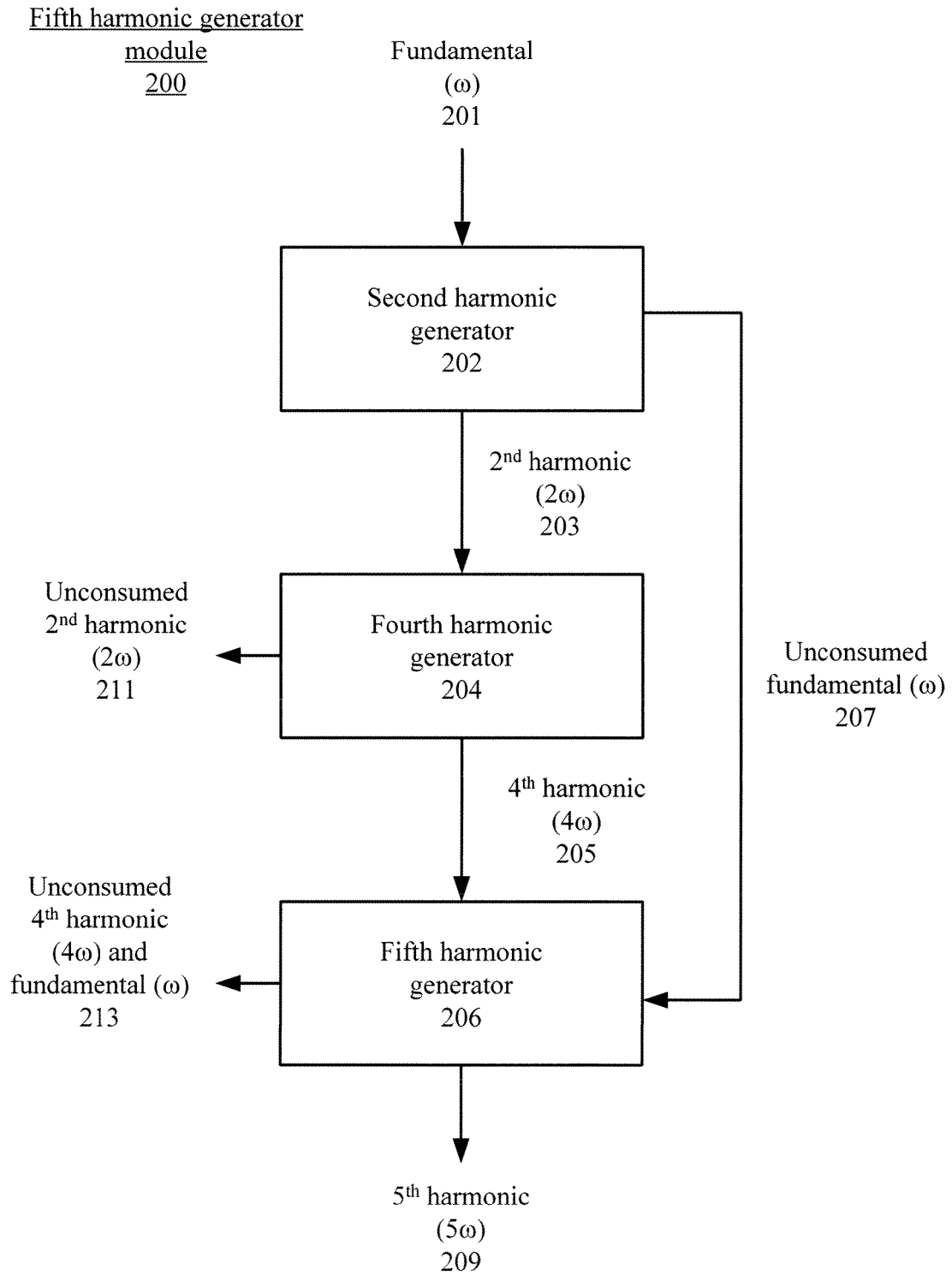
FIG. 2A illustrates an exemplary fifth harmonic generator module.
Figure 2B:
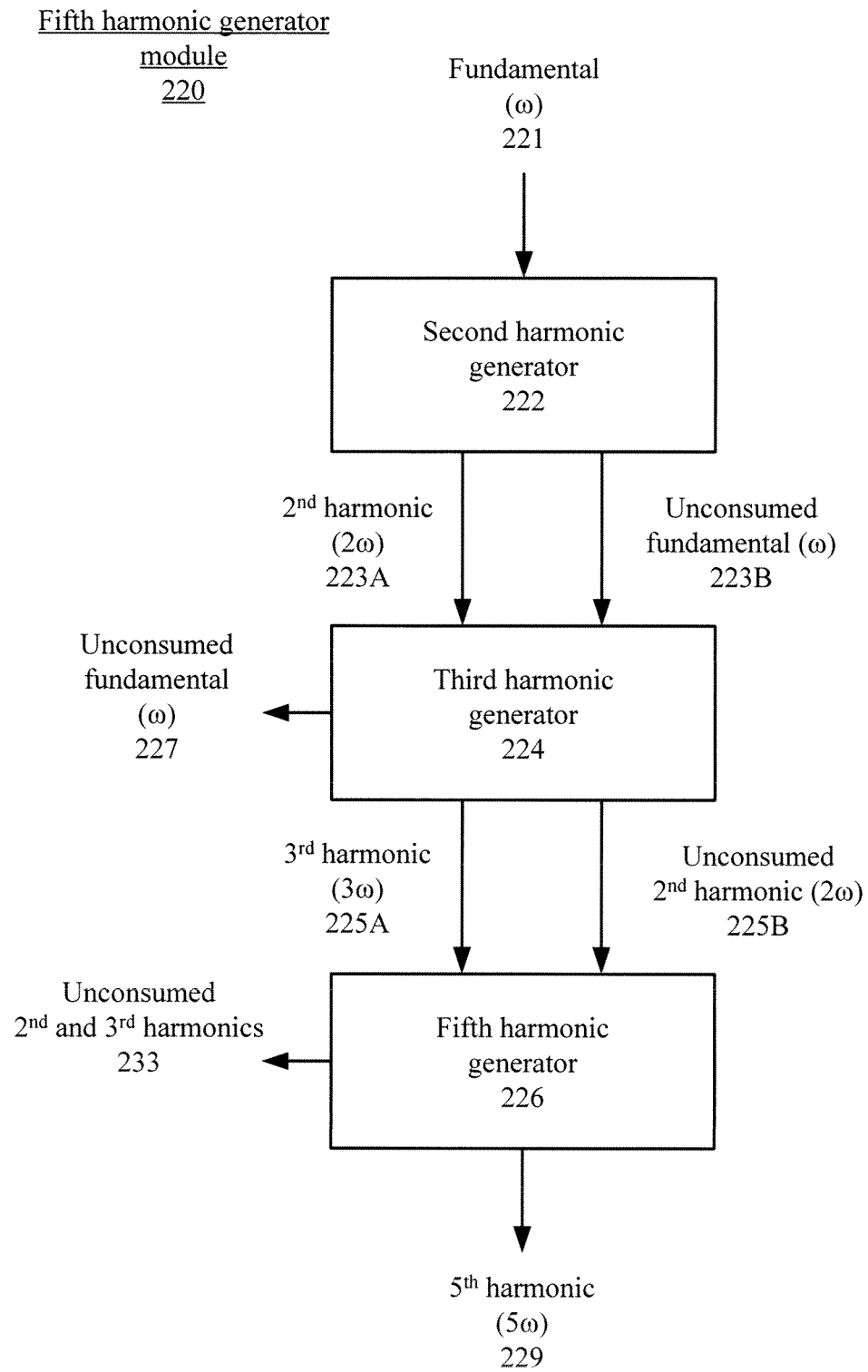
FIG. 2B illustrates an alternative exemplary fifth harmonic generator module.

FIG. 2A illustrates a simplified block diagram of an exemplary fifth harmonic generator module 200 suitable for performing the function of fifth harmonic generator module 105 (FIG. 1). In fifth harmonic generator module 200, the fundamental (ω) 201 is provided directly to a second harmonic generator 202, which generates second harmonic (2ω) 203. Note that a harmonic generator does not completely consume its input light, which is exploited in fifth harmonic generator module 200. Specifically, the fundamental (ω) not consumed by second harmonic generator 202 (i.e. an unconsumed fundamental (ω) 207) can be provided to a fifth harmonic generator 206.

In one embodiment (not shown), the unconsumed fundamental (ω) is allowed to propagate directly through second harmonic generator 202 and a fourth harmonic generator 204 to arrive at fifth harmonic generator 206 along with a fourth harmonic (4ω) 205 generated by fourth harmonic generator 204. This approach can be practical for pulse widths of about 10 ps or longer, which are the preferred pulse widths for the pump and fundamental lasers described herein. A pulse width of 10 ps in time means that the spatial length of the pulse is about 3 mm, and as a result, small differential delays in pulse propagation through second harmonic generator 202 and fourth harmonic generator 204 are generally not significant.

In another embodiment, the unconsumed fundamental (ω) 207 may be separated from the second harmonic (2ω) 203 at the output of second harmonic generator 202 and directed by components, for example, mirrors and prisms, to fifth harmonic generator 206. This approach allows optimization of the timing of the arrival of the pulses of the fundamental (ω) and the fourth harmonic (4ω) 205 at fifth harmonic generator 206, as well as allowing separate optimization of optics coatings, beam alignment, and beam waists.

Second harmonic generator 202 uses a non-linear crystal, preferably LBO (lithium triborate). LBO is non-critically phase matched for the XZ crystal plane for a wavelength near 1171 nm at a temperature of about 45° C., thereby resulting in insignificant walk off for temperatures near, or a little higher than 45° C. The crystal length can be selected to convert an appropriate fraction of fundamental (ω) 201 to second harmonic (2ω) 203 and to leave an appropriate amount of unconsumed fundamental (ω) 207 for fifth harmonic generator 206.

Second harmonic (2ω) 203 is directed to fourth harmonic generator 204, which generates fourth harmonic (4ω) 205. If desired, any unconsumed second harmonic (2ω) 211 may be separated out from fourth harmonic (4ω) 204 by, for example, a polarizing beam splitter. Unconsumed second harmonic 211 may also be recirculated in a cavity so that the unconsumed pulse is coincident with the next incoming pulse so as to increase the second harmonic power density in the crystal and more efficiently convert second harmonic (2ω) 203 to fourth harmonic (4ω) 205. An example of recirculating an input frequency is shown in FIG. 4 for frequency mixing module 400. A similar scheme to that shown in FIG. 4 could be used to recirculate second harmonic (2ω) 203 in fourth harmonic generator 204.

Fourth harmonic generator 204 uses a non-linear crystal, preferably CLBO or LBO. CLBO is critically phase matched for wavelengths near 585.5 nm at an angle of about 52.8° for a temperature near 120° C. with a walk-off angle of about 37 mrad and a $d_{eff}$ of about 0.7 pm V$^{-1}$. LBO is critically phase matched for wavelengths near 585.5 nm at angles between about 67.7° and 68.4° for the XY crystal plane at temperatures from less than 50° C. to over 200° C., with a low walk-off angle in the range of about 12 mrad to 14 mrad, but a $d_{eff}$ of about 0.3 pm V$^{-1}$, which is significantly lower than that of CLBO.

Fourth harmonic (4ω) 205 is directed to fifth harmonic generator 206, which generates fifth harmonic (5ω) 205 by mixing fourth harmonic (4ω) 205 with unconsumed fundamental (ω) 207 from second harmonic generator 202 in a non-linear crystal. If desired, any unconsumed fourth harmonic (4ω) and unconsumed fundamental (ω) (together labeled 213) may be separated out from the fifth harmonic by, for example, a prism or a polarizing beam splitter. Any unconsumed fundamental (ω) 207 may also be recirculated in a cavity so that the unconsumed pulse is coincident with the next incoming pulse so as to increase the fundamental power density in the crystal and more efficiently convert fourth harmonic (4ω) 205 to fifth harmonic (5ω) 209. As noted above, an example of recirculating an input frequency is shown in FIG. 4 for the frequency mixing module 400. A similar scheme to that shown in FIG. 4 could be used to recirculate unconsumed fundamental (ω) 207 in fifth harmonic generator 206.

In preferred embodiments, fifth harmonic generator 204 uses either CLBO or LBO as the non-linear crystal for the frequency mixing. CLBO is critically phase matched for wavelengths near 292.75 nm and 1171 nm at an angle of about 56.1° at a temperature of about 120° C., with a walk-off angle of about 38 mrad and a $d_{eff}$ of about 0.8 pm V$^{-1}$. LBO is critically phase matched for wavelengths near 292.75 nm and 1171 nm at angles between about 72.0° and 73.7° for the XY crystal plane at temperatures from less than 50° C. to over 200° C., with a low walk-off angle in the range of about 11 mrad to 13 mrad but a $d_{eff}$ of about 0.3 pm V$^{-1}$, which is significantly lower than that of CLBO. In one embodiment, fifth harmonic generator 206 uses a hydrogen-annealed CLBO or LBO crystal.

FIG. 2B illustrates a simplified block diagram of an exemplary alternative fifth harmonic generator module 220 suitable for performing the function of fifth harmonic generator module 105 (FIG. 1). Fifth harmonic generator 220 has an advantage over the fifth harmonic generator 200 in that fifth harmonic generator 220 can use a nearly non-critical phase matching for its fifth harmonic generator 226 compared with critical phase matching for fifth harmonic generator 206 of fifth harmonic generator module 200. Depending on the required output power level, laser repetition rate, laser pulse width, cost and other factors, either module 200 or module 220 may be most suitable.

In fifth harmonic generator module 220, a fundamental (ω) 221 is provided directly to a second harmonic generator 222, which generates second harmonic (2ω) 223A in a manner similar to that described above for second harmonic generator 202 (FIG. 2A). Preferably, an LBO crystal is used for the non-linear crystal in a substantially similar manner to that described above for second harmonic generator 202.

As described above, not all of the input light is consumed by second harmonic generator 222. In fifth harmonic generator module 220, second harmonic generator 222 outputs second harmonic (2ω) 223A and an unconsumed fundamental (ω) 223B and directs them both to a third harmonic (3ω) generator 224. Lens, prisms, mirrors and other optical components can be used to refocus second harmonic (2ω) 223A and unconsumed fundamental (ω) 223B to a substantially coincident focus within the non-linear crystal of third harmonic generator 224. Appropriate optical materials may also be used, if needed, to introduce a small relative delay between second harmonic (2ω) 223A and unconsumed fundamental (ω) 223B to compensate for relative delays between the pulses caused by second harmonic generator 222, so that the pulses arrive substantially simultaneously at the non-linear crystal of third harmonic generator 224.

Third harmonic generator 224 generates a third harmonic (3ω) 225A by mixing second harmonic (2ω) 223A and fundamental (ω) 223B in a non-linear crystal. If desired, any unconsumed fundamental (ω) 227 may be separated out from third harmonic (3ω) 225A and unconsumed second harmonic (2ω) 225B, by, for example, a prism. Unconsumed fundamental (ω) 227 may also be recirculated in a cavity so that the unconsumed pulse is coincident with the next incoming pulse so as to increase the fundamental power density in the crystal and more efficiently convert second harmonic (ω) 223A to third harmonic (ω) 225A. An example of recirculating an input frequency is shown in FIG. 4 for frequency mixing module 400. A similar scheme to that shown in FIG. 4 could be used to recirculate unconsumed fundamental (ω) 227 in third harmonic generator 224.

In preferred embodiments, third harmonic generator 224 uses LBO as the non-linear crystal for frequency mixing. LBO is critically phase matched for type II mixing of wavelengths near 1171 nm and 585.5 nm at angles between about 22.7° and 34.9° for the YZ crystal plane at temperatures from less than 50° C. to over 200° C., with a low walk-off angle in the range of about 7 mrad to 10 mrad. LBO can also be critically phase matched for the XY plane for type I mixing, but the walk-off angle is a little larger (approximately 15 mrad), and the polarization of one input wavelengths has to rotated to align it to the other for type I mixing.

Third harmonic (3ω) 225A and unconsumed second harmonic (2ω) 225B are both directed to fifth harmonic generator 226, which generates fifth harmonic (5ω) 229 by mixing those frequencies together in a non-linear crystal. If desired, any unconsumed third harmonic and unconsumed second harmonic (together labeled 233) may be separated out from the fifth harmonic by, for example, a prism or a polarizing beam splitter. Any portion of second harmonic (2ω) 225B that is unconsumed may also be recirculated in a cavity so that the unconsumed pulse is coincident with the next incoming pulse so as to increase the second harmonic power density in the crystal and more efficiently convert the third harmonic (3ω) 225A to the fifth harmonic 229. An example of recirculating an input frequency is shown in FIG. 4 for the frequency mixing module 400. A similar scheme to that shown in FIG. 4 could be used to recirculate second harmonic (2ω) 225B in fifth harmonic generator 226.

In preferred embodiments of fifth harmonic generator 226, the non-linear crystal is CLBO, which is non-critically phase matched for wavelengths of 585.5 nm and 390.3 nm at a temperature of about 161° C. In such embodiments, the CLBO crystal can be used near non-critically phased matched at a temperature less than 161° C., such as about 120° C., or between about 80° C. and about 140° C., at an angle between about 85.1° and 87.4° with a low walk-off angle in the range of about 4 mrad to 7 mrad. In one embodiment, fifth harmonic generator 226 uses a hydrogen-annealed CLBO crystal.

Figure 3:
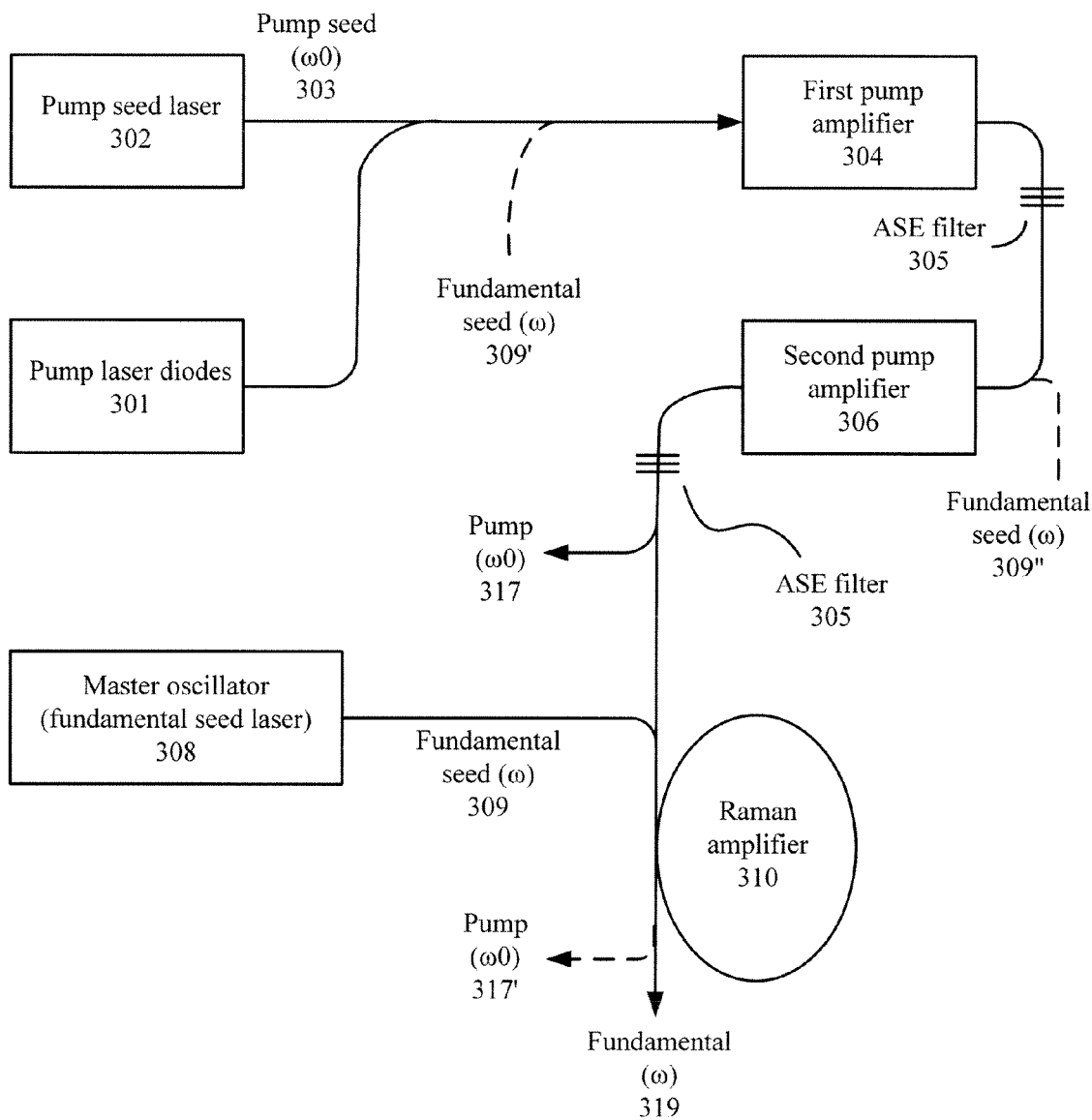
FIG. 3 illustrates exemplary pump and fundamental lasers for generating a pump wavelength of approximately 1109 nm.

FIG. 3 illustrates an exemplary embodiment of a pump laser and a fundamental laser 300. A pump seed laser 302 generates a pump seed 303 at the desired pump frequency (ω0) which, in preferred embodiments, corresponds to a wavelength of about 1109.1 nm. Pump seed laser 302 is preferably a stable, narrow-band laser with an E95 bandwidth less than about 300 pm, or, in some embodiments, less than 100 pm. In some embodiments, pump seed laser 302 is a stabilized diode laser, or a stabilized low-power fiber laser. In some embodiments, pump seed laser 302 is a CW laser. In other embodiments, pump seed laser 302 is a pulsed laser and is triggered in a synchrony with a master oscillator 308 and pump laser diodes 301.

Pump seed ($\omega$0) 303 is combined with shorter wavelength light from pump laser diodes 301. Preferably, pump laser diodes 301 output a wavelength between about 900 nm and about 1 µm, such as a wavelength near 975 nm. Pump laser diodes 301 may generate relatively broadband light over a wavelength range of about 1 nm or a few nm. The output from pump laser diodes 301 is combined with pump seed ($\omega$0) 303 and fed into a first pump amplifier 304. First pump amplifier 304 preferably comprises an Yb-doped optical fiber. First pump amplifier 304 amplifies pump seed ($\omega$0) 303 to a higher power level, such as from a few mW to a few hundred mW or a few W, or from about 100 mW to a few W. In some embodiments, the output of first pump amplifier 304 may be sent to a second pump amplifier 306 to further amplify the pump frequency ($\omega$0) to higher power levels. In some embodiments (not shown), additional amplifiers similar to second amplifier 306 may be daisy-chained to further increase the power at the pump frequency $\omega$0. In some embodiments, depending on the power needed at the near 193 nm output wavelength of the laser, the power at pump frequency $\omega$0 may be increased to a few W, or a few tens of W, or, in one embodiment, about 100 W. As indicated in FIG. 3, one or more ASE (amplified stimulated emission) filters 305 may be distributed within the amplifier chain (and/or within individual amplifiers) to suppress ASE and ensure that the output bandwidth is substantially similar to that of pump seed laser 302. A portion (such as less than 50%) of the amplified light at the pump frequency is separated out and directed to frequency mixing module 107 (FIG. 1). That portion of the amplified light at the pump frequency may be tapped off at the end of amplifier chain as pump 317, or separated out after a Raman amplifier as pump 317'. In some embodiments (not shown), the portion of the amplified light at the pump frequency may be tapped off part way along the amplifier chain.

In this embodiment, the amplifier light at the pump frequency is directed to Raman amplifier 310. Raman amplifier 310 generates a fundamental frequency ($\omega$) 319 by Raman amplification of a fundamental seed ($\omega$) 309 generated by master oscillator 308. Master oscillator 308 generates fundamental seed ($\omega$) 309 at the desired fundamental frequency $\omega$ and fundamental bandwidth, which is preferably an E95 bandwidth less than about 300 pm, or, in some embodiments, less than about 100 pm. In preferred embodiments, the frequency $\omega$ corresponds to a wavelength close to 1171 nm. Master oscillator 308 must be very stable as it primarily determines the overall stability of the fundamental seed laser. Fundamental seed ($\omega$) 309 may be combined with the amplified light at the pump frequency just before Raman amplifier 310, as shown in FIG. 3, or it may be injected earlier, such as within the amplifier daisy chain as shown as fundamental seed ($\omega$) 309'', or before the first pump amplifier as shown by fundamental seed ($\omega$) 309'. In one embodiment (not shown), the fundamental seed may be combined with pump seed 303, before pump seed 303 is combined with the light from pump laser diodes 301. This configuration has the advantage of combining only low power light before the high power of the laser diodes is combined. More details of different schemes for combining the seed for a Raman amplifier with the pump light are described in U.S. patent application Ser. No. 14/022,190, entitled "Solid State Illumination Source And Inspection System", and filed on Nov. 15, 2013, which is incorporated by reference herein.

In preferred embodiments, Raman amplifier 310 comprises a fused silica fiber, or a germania-doped fused silica fiber. Because the Raman gain of fused silica and germania-doped fused silica is high, approximately 2 m of fiber or less may provide sufficient gain (depending on the power of master oscillator 308 and the desired output power of the fundamental 319). Because of the higher gain of germania-doped fused silica compared with pure fused silica, a shorter length fiber can be used if it is doped with germania. Because germania is hygroscopic, the germania doping level is preferably less than 30%, such as a doping level between about 10% and 20%.

Filters, such as fiber Bragg gratings (not shown) may be placed after Raman amplifier 310 to minimize the levels of pump light, light from the pump laser diodes, or light from ASE in fundamental ($\omega$) 319.

Because Raman fiber amplifiers have high gain over a relative broad bandwidth (approximately 200 cm$^{-1}$), in some embodiments, a fundamental wavelength slightly shifted from 1171 nm, for example a wavelength between about 1150 nm and about 1175 nm, may be generated from a pump wavelength near 1109 nm. Likewise a fundamental close to 1171 nm may be generated from pump wavelength slightly shifted from 1109 nm, such as a pump wavelength between about 1105 nm and about 1130 nm. Hence, various deep UV wavelengths between about 189 nm and about 200 nm may be generated by this laser by appropriate choices of fundamental $\omega$ and pump $\omega$0 taking into account the properties of the non-linear crystals used for frequency conversion.

FIG. 4 illustrates an exemplary frequency mixing module 400 that generates a laser output 409 (or alternatively a laser output 409') at a wavelength near 193 nm by mixing a fifth harmonic (5$\omega$) 401A with a pump ($\omega$0) 401B. Frequency mixing module 400 can perform the function of frequency mixing module 107 (FIG. 1).

In frequency mixing module 400, the input light comprising fifth harmonic (5$\omega$) 401A and pump ($\omega$0) 401B are combined by beam combining optics 410 and then directed towards, and focused, in a non-linear crystal 406. Optics 410 may comprise any combination of prisms, beam splitters, wave plates, and/or lenses to make the two input frequencies of light (401A and 401B) substantially collinear, adjust their planes of polarization to match the crystal (for example, for type I frequency mixing, the polarizations should be substantially aligned), and focus the two frequencies to substantially overlapping beam waists inside non-linear crystal 406. In preferred embodiments, non-linear crystal 406 has its input and output faces cut at the appropriate Brewster's angles to minimize reflection losses of fifth harmonic (5$\omega$) 401A and laser output 409 at the respective faces. In embodiments where the output face is cut at Brewster's angle, laser output 409 may be sufficiently separated from the other wavelengths by refraction at that surface. In alternative embodiments where the output face of crystal 406 is not at Brewster's angle, or where the angular separation of the frequencies is not large enough, a beam splitter 407' (such as a polarizing beam splitter) may be used to separate laser output 409'.

In one embodiment of frequency mixing module 400, non-linear crystal 406 is contained within an optical cavity that recirculates unconsumed pump frequency light 411 to increase the power density of the pump frequency in non-linear crystal 406, while using only a small portion of the total pump laser power for frequency mixing module 400.

Unconsumed pump (ω0) 411, after it leaves non-linear crystal 406 is reflected off mirrors 403, 404, and 405 so as to arrive at partially transmitting mirror 402 substantially coincident with the next arriving pump 401B pulse. Mirror 402 is coated such that it transmits the incoming laser pulses 401A and 401B, while reflecting the recirculating unconsumed pump 411. The total optical path length from the surface of mirror 402 back to the same surface should be equal to the spacing of incoming pulses, or a unit fraction (such as one half or one third) thereof, so that the recirculated pulses are coincident with the incoming pulses. For example, if the laser repetition rate is 100 MHz, then the optical path length of the cavity needs to be close to 2.998 m or 1.500 m. Although FIG. 4 shows a bow-tie ring cavity, any optical cavity, ring or linear, known in the art can be used.

In another embodiment, unconsumed pump (ω0) 411 is not recirculated. In such an embodiment, mirrors 402, 403, 404, and 405 are omitted, and unconsumed pump (ω0) 411 will be directed to a beam dump (not shown) after non-linear crystal 406.

Any unconsumed fifth harmonic (5ω) 413 may be dumped after non-linear crystal 406. Because a high power level of the pump frequency inside the crystal can be achieved by the recirculation of unconsumed pump 411, those embodiments that recirculate unconsumed pump 411 typically can consume essentially all of the fifth harmonic in the frequency conversion process in non-linear crystal 406 by choosing an appropriate length for non-linear crystal 406.

In one embodiment, non-linear crystal 406, or non-linear crystal 406 and beam splitter 407, are scanned because, over time, the deep UV radiation damages those materials. The scanning may be a continuous slow scan, or may happen in discrete steps after a degradation of the output beam profile or intensity is detected. More information on scanning non-linear crystals can be found in U.S. Provisional Application 61/666,675, entitled "Scan rate for continuous motion of a crystal in a frequency converted laser", filed Jun. 29, 2012, and incorporated by reference herein.

As known by those skilled in the art, mirrors and prisms may be used to direct the light where needed within the laser and its various modules. Lenses and curved mirrors may be used to focus the beam waist to a point inside or proximate to the non-linear crystals where appropriate. Prisms, beam splitters, gratings, or other diffractive optical elements may be used to separate the different wavelengths at the outputs of each harmonic generator module when needed. Appropriately coated mirrors, beam splitters/combiners or prisms may be used to combine the different wavelengths at the input to the harmonic generators as appropriate.

TABLE 1 non-linear crystals and operating conditions

| Stage | Vacuum Wavelength | Crystal axis | Crystal type | Crystal plane | Temp (° C.) | Θ | Φ |
|---|---|---|---|---|---|---|---|
| 2nd harmonic generator | 1171 nm | e | LBO | X2 | 45 | 89.7° | 0.0° |
| 3rd harmonic generator | 1171 nm 585.5 nm | o e | LBO | Y2 | 100 | 27.2° | 90.0° |
| 4th harmonic generator | 585.5 nm | o | CLBO | N/A | 120 | 52.8° | N/A |
| 4th harmonic generator | 585.5 nm | o | LBO | XY | 200 | 90.0° | 68.4° |
| 5th (A) harmonic generator | 1171 nm 292.75 nm | o e | CLBO | N/A | 120 | 56.1° | N/A |
| 5th (A) harmonic generator | 1171 nm 292.75 nm | o o | LBO | XY | 200 | 90.0° | 73.7° |
| 5th (B) harmonic generator | 585.5 nm 390.3 nm | o o | CLBO | N/A | 120 | 86.5° | N/A |
| Frequency mixing module | 1109.1 nm 234.2 nm | o o | CLBO | N/A | 120 | 85.6° | N/A |

Table 1 above summarizes some of the suitable non-linear crystals and operating conditions for each of the frequency conversion steps. Fifth (A) harmonic generator refers to fifth harmonic generator 206 of FIG. 2A, whereas fifth harmonic (B) generator refers to fifth harmonic generator 226 of FIG. 2B. Both LBO and CLBO are potentially suitable for the fourth harmonic generator, and for the fifth harmonic (A) generator. Note that other crystals (including LBO, CLBO and beta barium borate, BBO) or alternative orientations of LBO may be substituted in some stages without departing from the scope of this invention. As would be understood by one skilled in the art, the crystals in Table 1 can be operated at temperatures many degrees different than those listed as long as a corresponding change is made to the angles. The choice of crystal and operating temperature has to take into account many factors including the walk-off angle, the conversion efficiency, damage (particularly for those stages using or generating deep UV radiation), protection from absorption of moisture (for hygroscopic materials such as LBO and CLBO), and the cost and availability of crystals of the appropriate quality and size.

Any of the harmonic generators or frequency mixing modules may use some, or all, of the methods and systems disclosed in U.S. patent application Ser. No. 13/412,564, entitled "Laser with High Quality, Stable Output Beam, and Long Life High Conversion Efficiency Non-Linear Crystal", filed Mar. 5, 2012, and incorporated by reference herein.

FIGS. 5-11 illustrate systems that can include the above-described lasers that generate wavelengths near 193 nm using a pump wavelength near 1109 nm and a fundamental wavelength near 1171 nm. These systems can be used in photomask, reticle, wafer, and other inspection applications.

In accordance with certain embodiments, an inspection system is described that incorporates a laser operating at a wavelength near 193 nm. That inspection system may simultaneously detect two channels of data on a single detector. Such an inspection system may be used to inspect a substrate such as a reticle, a photomask, or a wafer, and may operate as described in U.S. Pat. No. 7,528,943, which issued on May 15, 2009 to Brown et al., and is incorporated by reference herein.

Figure 5:
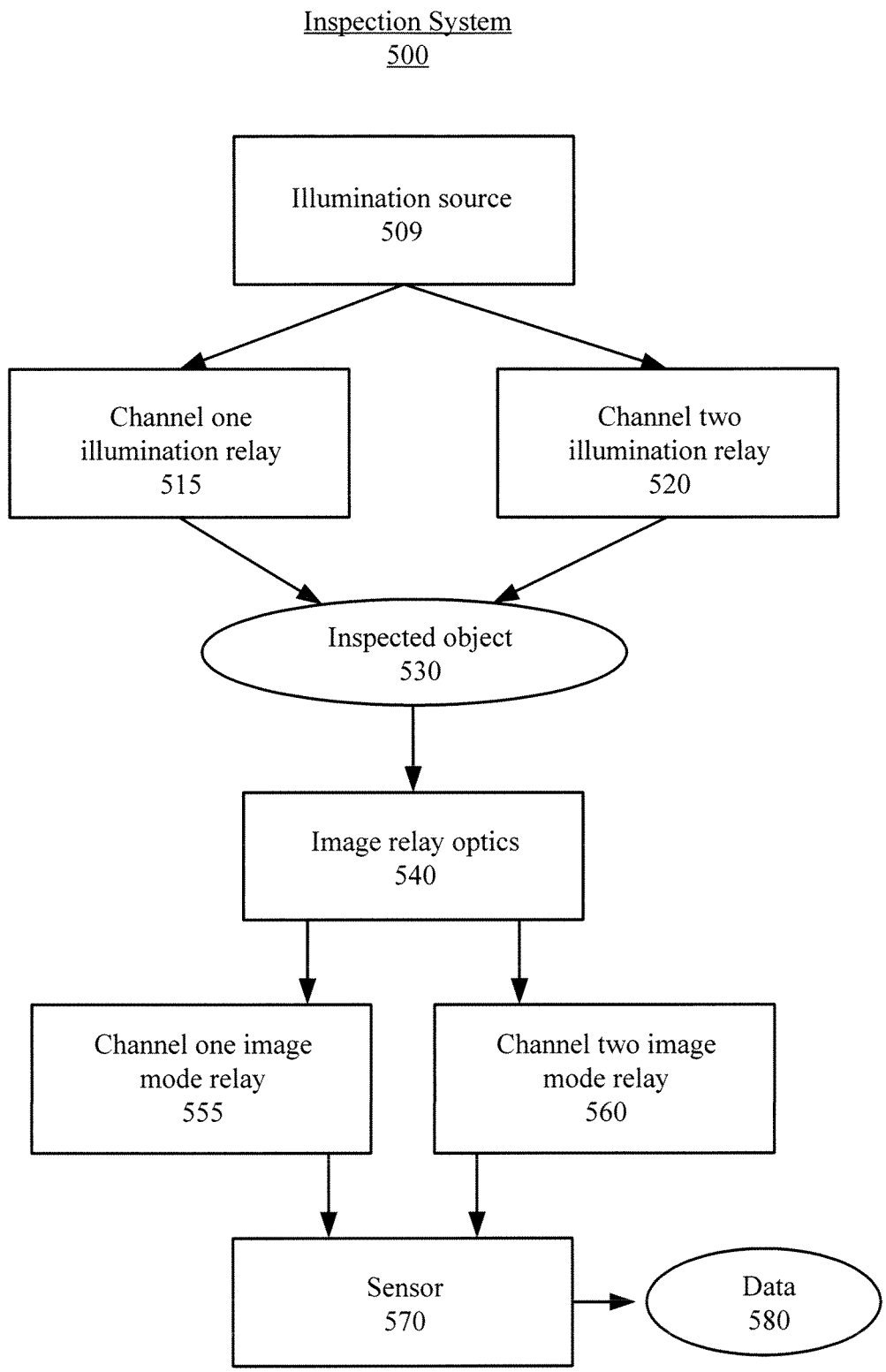
FIG. 5 illustrates exemplary inspection system that simultaneously collects two channels of image or signal data and that incorporates a 193 nm laser.

FIG. 5 illustrates an exemplary reticle, photomask, or wafer inspection system 500 that simultaneously detects two channels of image or signal on one sensor 570. The illumination source 509 incorporates a 193 nm laser as described herein. The light source may further comprise a pulse multiplier and/or a coherence reducing scheme. The two channels may comprise reflected and transmitted intensity when an inspected object 530 is transparent (for example a reticle or photomask), or may comprise two different illumination modes, such as angles of incidence, polarization states, wavelength ranges or some combination thereof.

As shown in FIG. 5, illumination relay optics 515 and 520 relay the illumination from source 509 to the inspected object 530. Inspected object 530 may be a reticle, a photomask, a semiconductor wafer, or other article to be inspected. Image relay optics 555 and 560 relay the light that is reflected and/or transmitted by inspected object 530 to sensor 570. The data corresponding to the detected signals or images for the two channels is shown as data 580 and is read out by circuitry configured to read the first channel and the second channel simultaneously and transmit the data to a computer (not shown) for processing.

Figure 6:
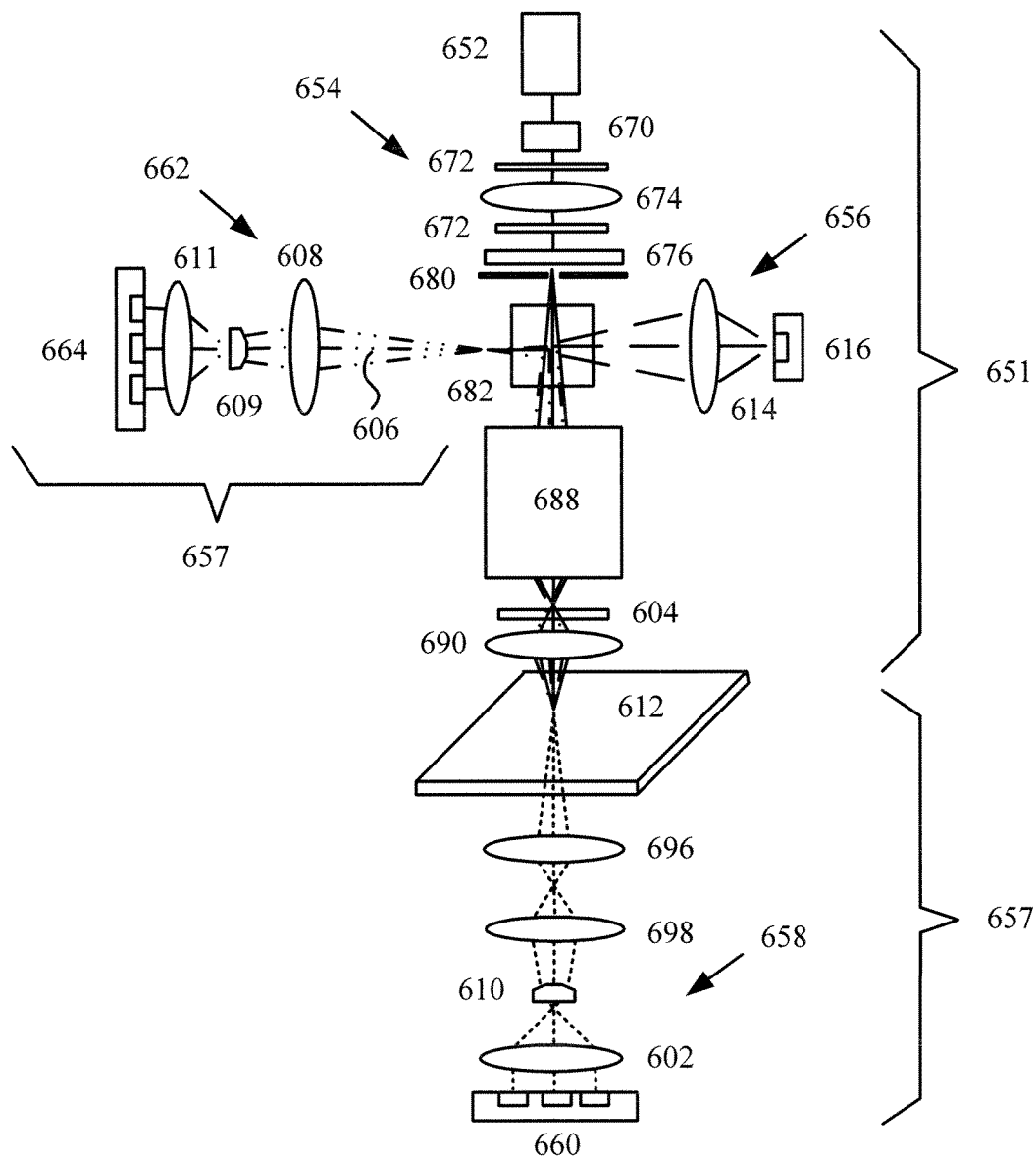
FIG. 6 illustrates an exemplary photomask or reticle inspection system that incorporates a 193 nm laser.

FIG. 6 illustrates an exemplary optical inspection system 600 for inspecting the surface of a substrate 612. System 600 generally includes a first optical arrangement 651 and a second optical arrangement 657. As shown, first optical arrangement 651 includes at least a light source 652, inspection optics 654, and reference optics 656, while the second optical arrangement 657 includes at least transmitted light optics 658, transmitted light detectors 660, reflected light optics 662, and reflected light detectors 664. In one preferred configuration, light source 652 includes one of the above-described improved lasers.

Light source 652 is configured to emit a light beam that passes through an acousto-optic device 670, which is arranged for deflecting and focusing the light beam. Light source 652 includes one of the 193 nm lasers described herein. Acousto-optic device 670 may include a pair of acousto-optic elements, e.g. an acousto-optic pre-scanner and an acousto-optic scanner, which deflect the light beam in the Y-direction and focus it in the Z-direction. By way of example, most acousto-optic devices operate by sending an RF signal to quartz or a crystal such as $TeO_2$. This RF signal causes a sound wave to travel through the crystal. Because of the travelling sound wave, the crystal becomes asymmetric, which causes the index of refraction to change throughout the crystal. This change causes incident beams to form a focused travelling spot which is deflected in an oscillatory fashion.

When the light beam emerges from acousto-optic device 670, it then passes through a pair of quarter wave plates 672 and a relay lens 674. Relay lens 674 is arranged to collimate the light beam. The collimated light beam then continues on its path until it reaches a diffraction grating 676. Diffraction grating 676 is arranged for flaring out the light beam, and more particularly for separating the light beam into three distinct beams, which are spatially distinguishable from one another (i.e. spatially distinct). In most cases, the spatially distinct beams are also arranged to be equally spaced apart and have substantially equal light intensities.

Upon leaving the diffraction grating 676, the three beams pass through an aperture 680 and then continue until they reach a beam splitter cube 682. Beam splitter cube 682 (in combination with the quarter wave plates 672) is arranged to divide the beams into two paths, i.e. one directed downward and the other directed to the right (in the configuration shown in FIG. 6). The path directed downward is used to distribute a first light portion of the beams to substrate 612, whereas the path directed to the right is used to distribute a second light portion of the beams to reference optics 656. In most embodiments, most of the light is distributed to substrate 612 and a small percentage of the light is distributed to reference optics 656, although the percentage ratios may vary according to the specific design of each optical inspection system. In one embodiment, reference optics 656 can include a reference collection lens 614 and a reference detector 616. Reference collection lens 614 is arranged to collect and direct the portion of the beams on reference detector 616, which is arranged to measure the intensity of the light. Reference optics are generally well known in the art and for the sake of brevity will not be discussed in detail.

The three beams directed downward from beam splitter 682 are received by a telescope 688, which includes several lens elements that redirect and expand the light. In one embodiment, telescope 688 is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From telescope 688, the three beams pass through an objective lens 690, which is arranged for focusing the beams onto the surface of substrate 612. As the beams intersect the surface as three distinct spots, both reflected light beams and transmitted light beams may be generated. The transmitted light beams pass through substrate 612, while the reflected light beams reflect off the surface. By way of example, the reflected light beams may reflect off of opaque surfaces of the substrate, and the transmitted light beams may transmit through transparent areas of the substrate. The transmitted light beams are collected by transmitted light optics 658 and the reflected light beams are collected by reflected light optics 662.

With regards to transmitted light optics 658, the transmitted light beams, after passing through substrate 612, are collected by a first transmitted lens 696 and focused with the aid of a spherical aberration corrector lens 698 onto a transmitted prism 610. Prism 610 can be configured to have a facet for each of the transmitted light beams that are arranged for repositioning and bending the transmitted light beams. In most cases, prism 610 is used to separate the beams so that they each fall on a single detector in transmitted light detector arrangement 660 (shown as having three distinct detectors). Accordingly, when the beams leave prism 610, they pass through a second transmitted lens 602, which individually focuses each of the separated beams onto one of the three detectors, each of which is arranged for measuring the intensity of the transmitted light.

With regards to reflected light optics 662, the reflected light beams after reflecting off of substrate 612 are collected by objective lens 690, which then directs the beams towards telescope 688. Before reaching telescope 688, the beams also pass through a quarter wave plate 604. In general terms, objective lens 690 and telescope 688 manipulate the collected beams in a manner that is optically reverse in relation to how the incident beams are manipulated. That is, objective lens 690 re-collimates the beams, and telescope 688 reduces their size. When the beams leave telescope 688, they continue (backwards) until they reach beam splitter cube 682. Beam splitter 682 is configured to work with quarter wave-plate 604 to direct the beams onto a central path 606.

The beams continuing on path 606 are then collected by a first reflected lens 608, which focuses each of the beams onto a reflected prism 609, which includes a facet for each of the reflected light beams. Reflected prism 609 is arranged for repositioning and bending the reflected light beams. Similar to transmitted prism 610, reflected prism 609 is used to separate the beams so that they each fall on a single detector in the reflected light detector arrangement 664. As shown, reflected light detector arrangement 664 includes three individually distinct detectors. When the beams leave reflected prism 609, they pass through a second reflected lens 611, which individually focuses each of the separated beams onto one of these detectors, each of which is arranged for measuring the intensity of the reflected light.

There are multiple inspection modes that can be facilitated by the aforementioned optical assembly. By way of example, the optical assembly can facilitate a transmitted light inspection mode, a reflected light inspection mode, and a simultaneous inspection mode. With regards to the transmitted light inspection mode, transmission mode detection is typically used for defect detection on substrates such as conventional optical masks having transparent areas and opaque areas. As the light beams scan the mask (or substrate 612), the light penetrates the mask at transparent points and is detected by the transmitted light detectors 660, which are located behind the mask and which measure the intensity of each of the light beams collected by transmitted light optics 658 including first transmitted lens 696, second transmitted lens 802, spherical aberration lens 698, and prism 610.

With regards to the reflected light inspection mode, reflected light inspection can be performed on transparent or opaque substrates that contain image information in the form of chromium, developed photoresist or other features. Light reflected by the substrate 612 passes backwards along the same optical path as inspection optics 654, but is then diverted by a polarizing beam splitter 682 into detectors 664. More particularly, first reflected lens 608, prism 609, and second reflected lens 611 project the light from the diverted light beams onto detectors 664. Reflected light inspection may also be used to detect contamination on top of opaque substrate surfaces.

With regards to the simultaneous inspection mode, both transmitted light and reflected light are utilized to determine the existence and/or type of a defect. The two measured values of the system are the intensity of the light beams transmitted through substrate 612 as sensed by transmitted light detectors 660 and the intensity of the reflected light beams as detected by reflected light detectors 664. Those two measured values can then be processed to determine the type of defect, if any, at a corresponding point on substrate 612.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect were examined. In addition, one may determine signatures for certain types of defects, such as the ratio of their reflected and transmitted light intensities. This information can then be used to automatically classify defects. U.S. Pat. No. 5,563,702, which issued on Apr. 1, 2008 and is incorporated by reference herein, describes additional details regarding inspection system 600.

Figure 7A:
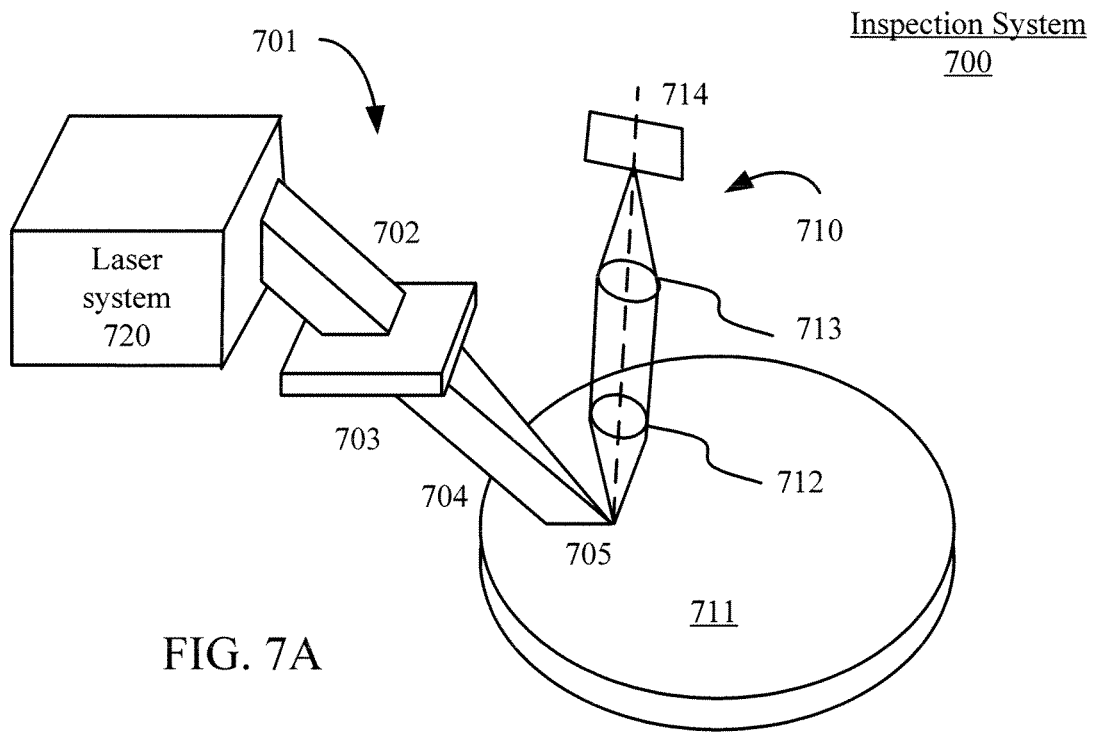
FIGS. 7A and 7B illustrate exemplary inspection systems with multiple collection optics and the 193 nm laser.

FIG. 7A illustrates an exemplary surface inspection system 700 that includes illumination system 701 and collection system 710 for inspecting areas of surface 711. As shown in FIG. 7A, a laser system 720 directs a light beam 702 through a lens 703. In a preferred embodiment, laser system 720 includes the above-described laser, an annealed crystal, and a housing to maintain the annealed condition of the crystal. First beam shaping optics can be configured to receive a beam from the laser and focus the beam to an elliptical cross section at a beam waist in or proximate to the crystal.

Lens 703 is oriented so that its principal plane is substantially parallel to a sample surface 711 and, as a result, illumination line 705 is formed on surface 711 in the focal plane of lens 703. In addition, light beam 702 and focused beam 704 are directed at a non-orthogonal angle of incidence to surface 711. In particular, light beam 702 and focused beam 704 may be directed at an angle between about 1 degree and about 85 degrees from a normal direction to surface 711. In this manner, illumination line 705 is substantially in the plane of incidence of focused beam 704.

Collection system 710 includes lens 712 for collecting light scattered from illumination line 705 and lens 713 for focusing the light coming out of lens 712 onto a device, such as charge coupled device (CCD) 714, comprising an array of light sensitive detectors. In one embodiment, CCD 714 may include a linear array of detectors. In such cases, the linear array of detectors within CCD 714 can be oriented parallel to illumination line 705. In one embodiment, multiple collection systems can be included, wherein each of the collection systems includes similar components, but differ in orientation.

Figure 7B:
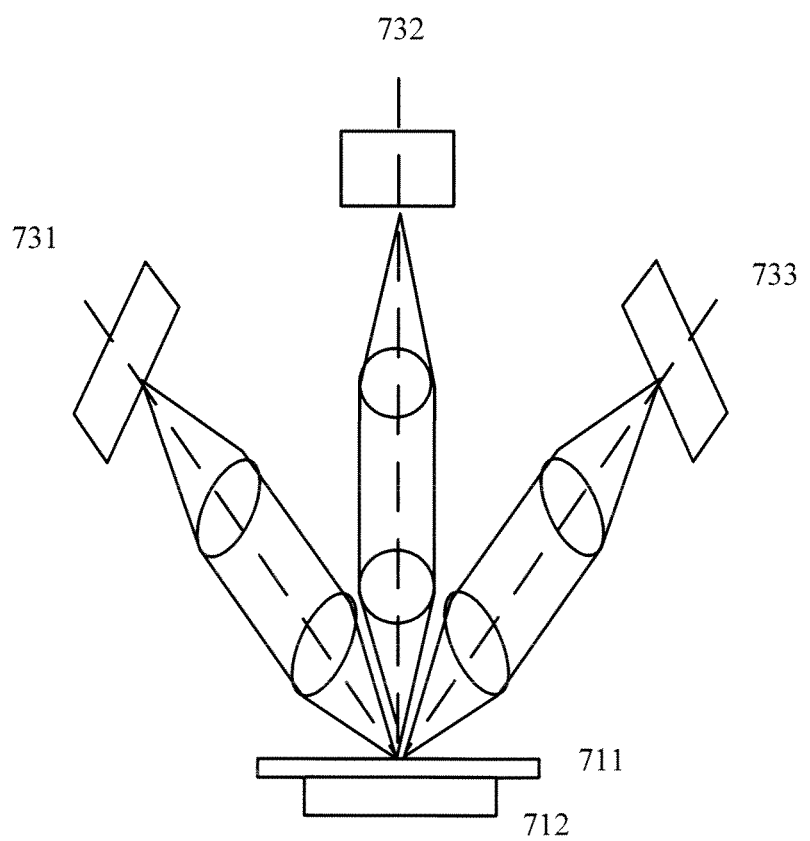

For example, FIG. 7B illustrates an exemplary array of collection systems 731, 732, and 733 for a surface inspection system (wherein its illumination system, e.g. similar to that of illumination system 701, is not shown for simplicity). First optics in collection system 731 collect light scattered in a first direction from the surface of sample 711. Second optics in collection system 732 collect light scattered in a second direction from the surface of sample 711. Third optics in collection system 733 collect light scattered in a third direction from the surface of sample 711. Note that the first, second, and third paths are at different angles of reflection to said surface of sample 711. A platform 712 supporting sample 711 can be used to cause relative motion between the optics and sample 711 so that the whole surface of sample 711 can be scanned. U.S. Pat. No. 7,525,649, which issued on Apr. 28, 2009 and is incorporated by reference herein, describes surface inspection apparatus 700 and other multiple collection systems in further detail.

Figure 8:
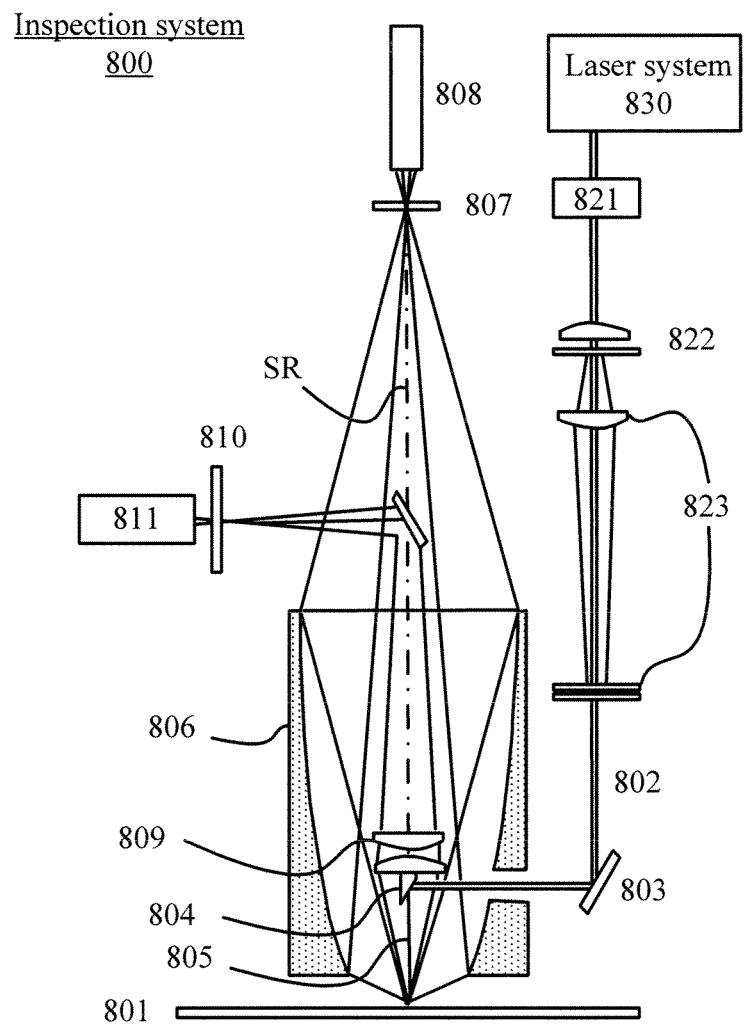
FIG. 8 illustrates an exemplary surface inspection system including the 193 nm laser.

FIG. 8 illustrates an exemplary surface inspection system 800 that can be used for inspecting anomalies on a surface 801. In this embodiment, surface 801 can be illuminated by a substantially stationary illumination device portion of a laser system 830 comprising a laser beam generated by the above-described laser generating a wavelength between about 189 nm and 200 nm. The output of laser system 830 can be consecutively passed through polarizing optics 821, a beam expander and aperture 822, and beam-forming optics 823 to expand and focus the beam.

The resulting focused laser beam 802 is then reflected by a beam folding component 803 and a beam deflector 804 to direct the beam 805 towards surface 801 for illuminating the surface. In a preferred embodiment, beam 805 is substantially normal or perpendicular to surface 801, although in other embodiments beam 805 may be at an oblique angle to surface 801.

In one embodiment, beam 805 is substantially perpendicular or normal to surface 801 and beam deflector 804 reflects the specular reflection of the beam from surface 801 towards beam turning component 803, thereby acting as a shield to prevent the specular reflection from reaching the detectors. The direction of the specular reflection is along line SR, which is normal to the surface 801 of the sample. In one embodiment where beam 805 is normal to surface 801, this line SR coincides with the direction of illuminating beam 805, where this common reference line or direction is referred to herein as the axis of inspection system 800. Where beam 805 is at an oblique angle to surface 801, the direction of specular reflection SR would not coincide with the incoming direction of beam 805; in such instance, the line SR indicating the direction of the surface normal is referred to as the principal axis of the collection portion of inspection system 800.

Light scattered by small particles is collected by mirror 806 and directed towards aperture 807 and detector 808. Light scattered by large particles are collected by lenses 809 and directed towards aperture 810 and detector 811. Note that some large particles will scatter light that is also collected and directed to detector 808, and similarly some small particles will scatter light that is also collected and directed to detector 811, but such light is of relatively low intensity compared to the intensity of scattered light the respective detector is designed to detect. In one embodiment, detector 811 can include an array of light sensitive elements, wherein each light sensitive element of the array of light sensitive elements is configured to detect a corresponding portion of a magnified image of the illumination line. In one embodiment, inspection system can be configured for use in detecting defects on unpatterned wafers. U.S. Pat. No. 6,271,916, which issued on Aug. 7, 2011 and is incorporated by reference herein, describes inspection system 800 in further detail.

Figure 9:
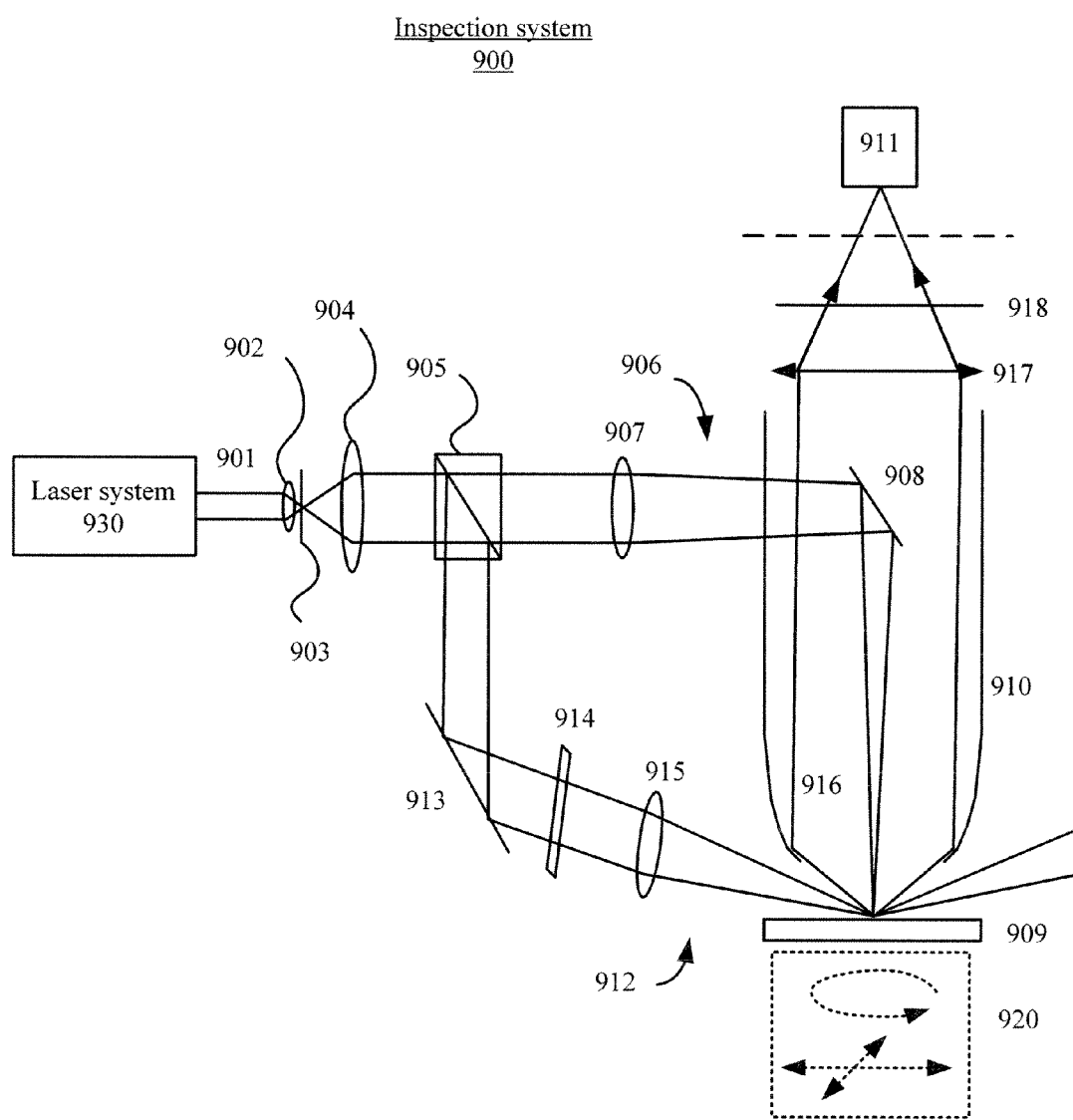
FIG. 9 illustrates another exemplary surface inspection system including the 193 nm laser.

FIG. 9 illustrates an exemplary inspection system 900 configured to implement anomaly detection using both normal and oblique illumination beams. In this configuration, a laser system 930, which includes the above-described laser generating a wavelength between about 189 nm and 200 nm, can provide a laser beam 901. A lens 902 focuses the beam 901 through a spatial filter 903 and lens 904 collimates the beam and conveys it to a polarizing beam splitter 905. Beam splitter 905 passes a first polarized component to the normal illumination channel and a second polarized component to the oblique illumination channel, where the first and second components are orthogonal. In the normal illumination channel 906, the first polarized component is focused by optics 907 and reflected by mirror 908 towards a surface of a sample 909. The radiation scattered by sample 909 is collected and focused by a paraboloidal mirror 910 to a photomultiplier tube 911.

In the oblique illumination channel 912, the second polarized component is reflected by beam splitter 905 to a mirror 913 which reflects such beam through a half-wave plate 914 and focused by optics 915 to sample 909. Radiation originating from the oblique illumination beam in the oblique channel 912 and scattered by sample 909 is also collected by paraboloidal mirror 910 and focused to photomultiplier tube 911. Note that photomultiplier tube 911 has a pinhole entrance. The pinhole and the illuminated spot (from the normal and oblique illumination channels on surface 909) are preferably at the foci of the paraboloidal mirror 910.

The paraboloidal mirror 910 collimates the scattered radiation from sample 909 into a collimated beam 916. Collimated beam 916 is then focused by an objective 917 and through an analyzer 918 to the photomultiplier tube 911. Note that curved mirrored surfaces having shapes other than paraboloidal shapes may also be used. An instrument 920 can provide relative motion between the beams and sample 909 so that spots are scanned across the surface of sample 909. U.S. Pat. No. 6,201,601, which issued on Mar. 13, 2001 and is incorporated by reference herein, describes inspection system 900 in further detail.

Figure 10:
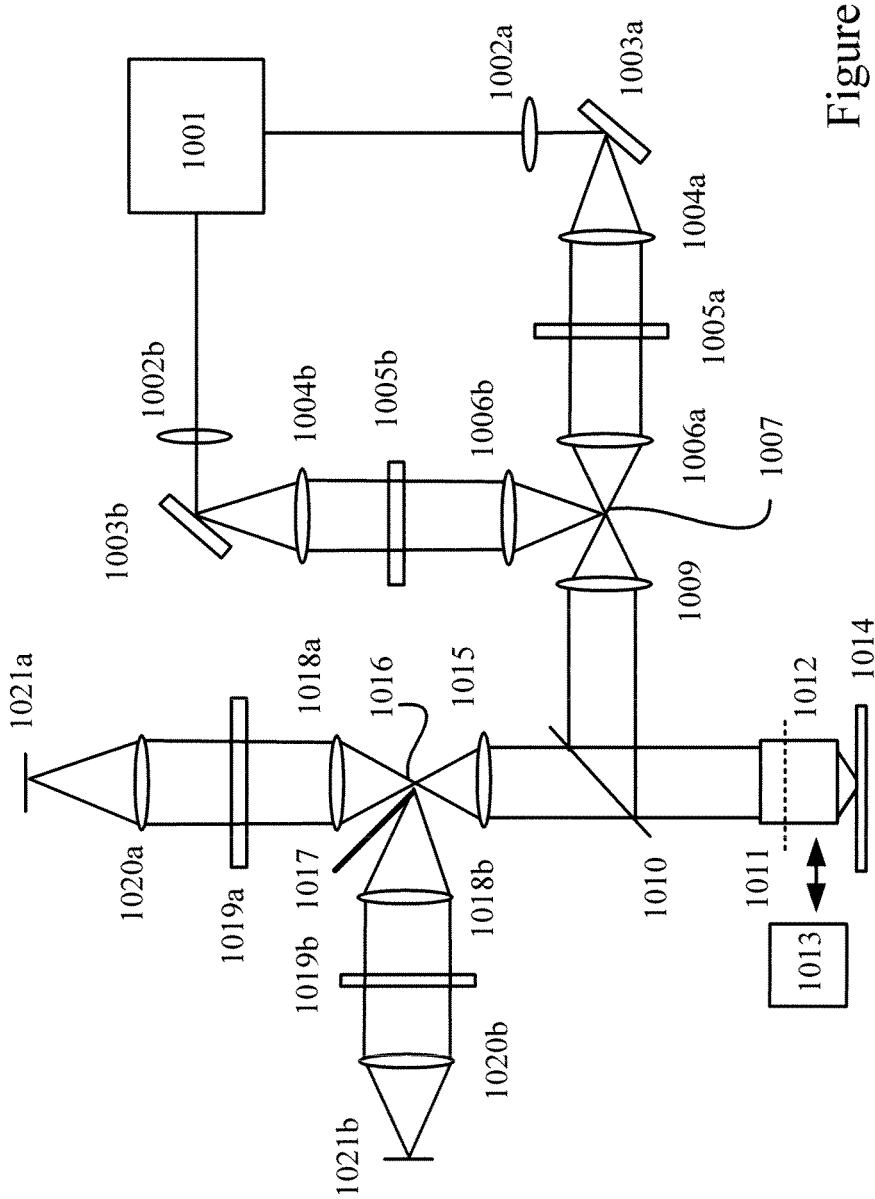
FIG. 10 illustrates an exemplary inspection system including multiple objectives and the 193 nm laser.

FIG. 10 illustrates an exemplary inspection system 1000 including multiple objectives and one of the above-described lasers. In system 1000, illumination from a laser source 1001 is sent to multiple sections of the illumination subsystem. Laser source 1001 includes one of the above-described lasers generating light at a wavelength between about 189 nm and about 200 nm. A first section of the illumination subsystem includes elements 1002a through 1006a. Lens 1002a focuses light from laser 1001. Light from lens 1002a then reflects from mirror 1003a. Mirror 1003a is placed at this location for the purposes of illustration, and may be positioned elsewhere. Light from mirror 1003a is then collected by lens 1004a, which forms illumination pupil plane 1005a. An aperture, filter, or other device to modify the light may be placed in pupil plane 1005a depending on the requirements of the inspection mode. Light from pupil plane 1005a then passes through lens 1006a and forms illumination field plane 1007.

A second section of the illumination subsystem includes elements 1002b through 1006b. Lens 1002b focuses light from laser 1001. Light from lens 1002b then reflects from mirror 1003b. Light from mirror 1003b is then collected by lens 1004b which forms illumination pupil plane 1005b. An aperture, filter, or other device to modify the light may be placed in pupil plane 1005b depending on the requirements of the inspection mode. Light from pupil plane 1005b then passes through lens 1006b and forms illumination field plane 1007. The light from the second section is then redirected by mirror or reflective surface such that the illumination field light energy at illumination field plane 1007 is comprised of the combined illumination sections.

Field plane light is then collected by lens 1009 before reflecting off a beamsplitter 1010. Lenses 1006a and 1009 form an image of first illumination pupil plane 1005a at objective pupil plane 1011. Likewise, lenses 1006b and 1009 form an image of second illumination pupil plane 1005b at objective pupil plane 1011. An objective 1012 (or alternatively 1013) then takes the pupil light and forms an image of illumination field 1007 at sample 1014. Objective 1012 or objective 1013 can be positioned in proximity to sample 1014. Sample 1014 can move on a stage (not shown), which positions the sample in the desired location. Light reflected and scattered from the sample 1014 is collected by the high NA catadioptric objective 1012 or objective 1013. After forming a reflected light pupil at objective pupil plane 1011, light energy passes beamsplitter 1010 and lens 1015 before forming an internal field 1016 in the imaging subsystem. This internal imaging field is an image of sample 1014 and correspondingly illumination field 1007. This field may be spatially separated into multiple fields corresponding to the illumination fields. Each of these fields can support a separate imaging mode.

One of these fields can be redirected using mirror 1017. The redirected light then passes through lens 1018b before forming another imaging pupil 1019b. This imaging pupil is an image of pupil 1011 and correspondingly illumination pupil 1005b. An aperture, filter, or other device to modify the light may be placed in pupil plane 1019b depending on the requirements of the inspection mode. Light from pupil plane 1019b then passes through lens 1020b and forms an image on sensor 1021b. In a similar manner, light passing by mirror or reflective surface 1017 is collected by lens 1018a and forms imaging pupil 1019a. Light from imaging pupil 1019a is then collected by lens 1020a before forming an image on detector 1021a. Light imaged on detector 1021a can be used for a different imaging mode from the light imaged on sensor 1021b.

The illumination subsystem employed in system 1000 is composed of laser source 1001, collection optics 1002-1004, beam shaping components placed in proximity to a pupil plane 1005, and relay optics 1006 and 1009. An internal field plane 1007 is located between lenses 1006 and 1009. In one preferred configuration, laser source 1001 can include one of the above-described lasers.

With respect to laser source 1001, while illustrated as a single uniform block having two points or angles of transmission, in reality this represents a laser source able to provide two channels of illumination, for example a first channel of light energy such as laser light energy at a first frequency which passes through elements 1002a-1006a, and a second channel of light energy such as laser light energy at a second frequency which passes through elements 1002b-1006b. Different light illumination and detection modes may be employed, such as a bright field mode in one channel and a dark field mode in the other channel.

While light energy from laser source 1001 is shown to be emitted 90 degrees apart, and the elements 1002a-1006a and 1002b-1006b are oriented at 90 degree angles, in reality light may be emitted at various orientations, not necessarily in two dimensions, and the components may be oriented differently than as shown. FIG. 10 is therefore simply a representation of the components employed and the angles or distances shown are not to scale nor specifically required for the design.

Elements placed in proximity to pupil plane 1005 may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 1005a, 1005b, 1019a, and 1019b.

Multiple objectives may also be used as shown in FIG. 10. For example, although two objectives 1012 and 1013 are shown, any number is possible. Each objective in such a design may be optimized for each wavelength produced by laser source 1001. These objectives 1012 and 1013 can either have fixed positions or be moved into position in proximity to the sample 1014. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be higher. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 1015. The purpose of the image forming optics 1015 is to form an internal image 1016 of sample 1014. At this internal image 1016, a mirror 1017 can be placed to redirect light corresponding to one of the inspection modes. It is possible to redirect the light at this location because the light for the imaging modes are spatially separate. The image forming optics 1018 (1018a and 1018b) and 1020 (1020a and 1020b) can be implemented in several different forms including a varifocal zoom, multiple afocal tube lenses with focusing optics, or multiple image forming mag tubes. U.S. Published Application 2009/0180176, which published on Jul. 16, 2009 and is incorporated by reference herein, describes additional details regarding system 1000.

Figure 11:
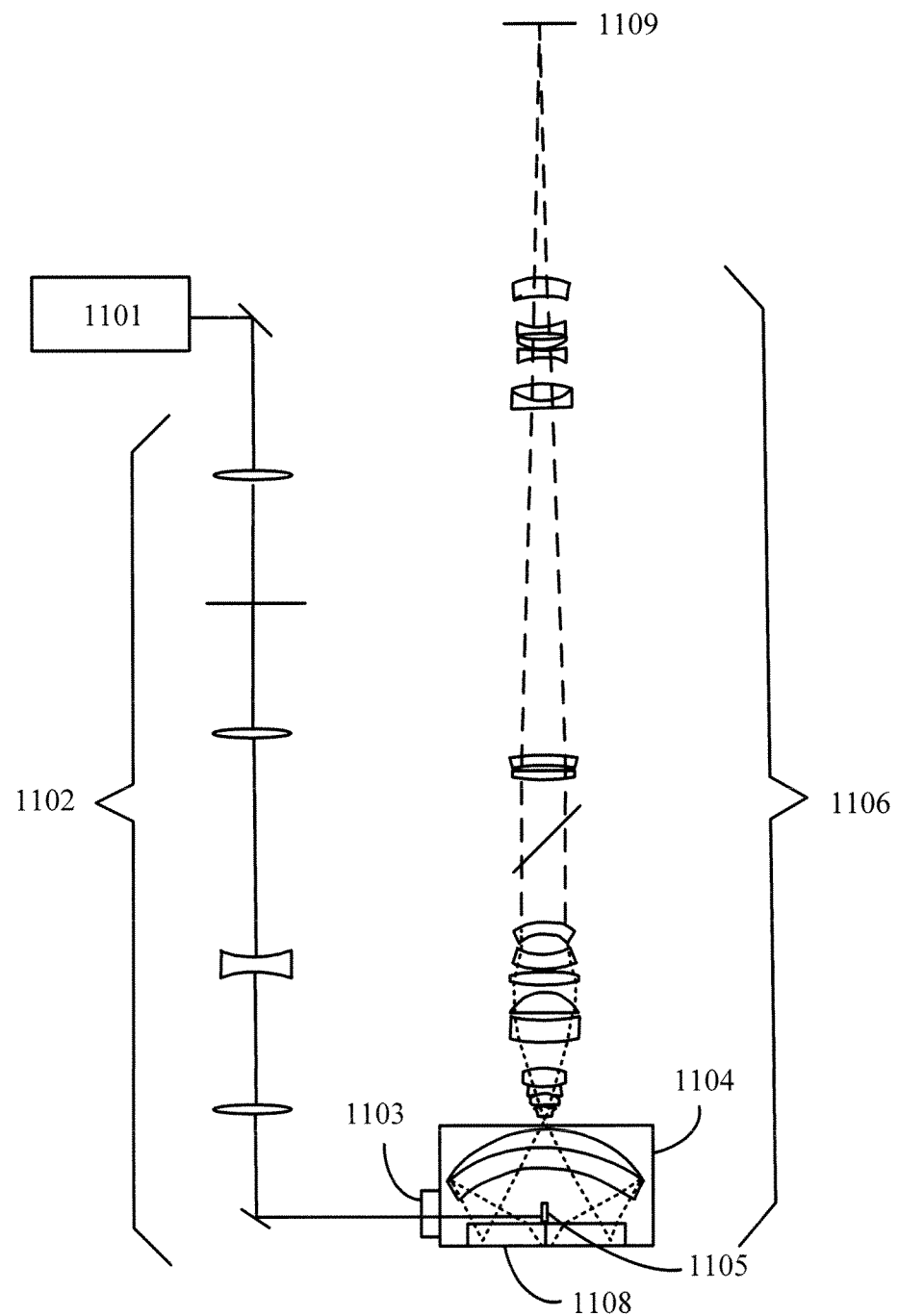
FIG. 11 illustrates an exemplary inspection system with dark-field and bright-field modes and including the 193 nm laser.

FIG. 11 illustrates the addition of a normal incidence laser dark-field illumination to a catadioptric imaging system 1100. The dark-field illumination includes a UV laser 1101, adaptation optics 1102 to control the illumination beam size and profile on the surface being inspected, an aperture and window 1103 in a mechanical housing 1104, and a prism 1105 to redirect the laser along the optical axis at normal incidence to the surface of a sample 1108. Prism 1105 also directs the specular reflection from surface features of sample 1108 and reflections from the optical surfaces of an objective 1106 along the optical path to an image plane 1109. Lenses for objective 1106 can be provided in the general form of a catadioptric objective, a focusing lens group, and a zooming tube lens section. In a preferred embodiment, laser 1101 can be implemented by the above-described lasers emitting a wavelength between about 189 nm and about 200 nm. U.S. Pat. No. 5,999,310, which issued on Dec. 7, 1999 and U.S. Publication 2007/0002465, which published on Jan. 4, 2007 describe system 1100 in further detail. Both the patent and the publication are incorporated by reference herein.

Other reticle, photomask, or wafer inspection systems can advantageously use the above-described improved laser. For example, other systems include those described in U.S. Pat. Nos. 5,563,702, 5,999,310, 6,201,601, 6,271,916, 7,352,457, 7,525,649, and 7,528,943. Yet further systems include those described in U.S. Publication 2009/0180176. When used in an inspection or metrology system, this improved laser may advantageously be combined with the coherence and speckle reducing apparatus and methods disclosed in published PCT application WO 2010/037106 and U.S. patent application Ser. No. 13/073,986. This improved laser may also be advantageously combined with the methods and systems disclosed in U.S. patent application Ser. No. 13/711,593, entitled "Semiconductor Inspection And Metrology System Using Laser Pulse Multiplier" filed Dec. 11, 2012, and in U.S. patent application Ser. No. 13/487,075, entitled "Semiconductor Inspection And Metrology System Using Laser Pulse Multiplier", filed on Jun. 1, 2012 and now published as U.S. Publication 2012/0314286 on Dec. 13, 2012, all of which are incorporated by reference herein.

The most critical part of a deep-UV laser is the final frequency conversion stage. The above-described laser generating a wavelength near 193 nm, which mixes the fifth harmonic of a fundamental near 1171 nm with a pump wavelength near 1109 nm, enables the use of substantially non-critical phase matching for that final frequency conversion. Near non-critical phase matching is more efficient and more stable than critical phase matching because a longer crystal can be used and because it is less affected by small changes in alignment. Note that the longer crystal also allows the use of lower peak power densities in the crystal while maintaining the same overall conversion efficiency, thereby slowing damage accumulation to the crystal. Notably, the herein described lasers are less complex and more efficient than eighth harmonic generation. Therefore, the above-described 193 nm laser, can provide significant system advantages during photomask, reticle, or wafer inspection and metrology.

Although the above describes an approximately 1171 nm fundamental wavelength and an approximately 1109.1 nm pump wavelength resulting in an output wavelength of 193.4 nm, it is to be understood that other wavelengths within a few nm of 193.4 nm could be generated by this approach using an appropriate choice of fundamental and pump wavelengths. Such lasers and systems utilizing such lasers are within the scope of this invention.

The various embodiments of the structures and methods of this invention that are described above are illustrative only of the principles of this invention and are not intended to limit the scope of the invention to the particular embodiments described. For example, non-linear crystals other than CLBO, LBO, or BBO or periodically-poled materials can be used for some of the frequency conversion stages. Thus, the invention is limited only by the following claims and their equivalents.

The invention claimed is:

1. A laser for generating light, the laser comprising:
   a pump laser configured to generate a pump frequency having a corresponding wavelength of between approximately 1105 nm and approximately 1130 nm;
   a fundamental laser configured to generate a fundamental frequency from a portion of the pump frequency, the fundamental frequency having a corresponding wavelength of between approximately 1150 nm and approximately 1175 nm;
   a fifth harmonic generator module configured to generate a fifth harmonic of the fundamental frequency; and
   a frequency mixing module configured to combine the pump frequency and the fifth harmonic frequency to generate an output wavelength between approximately 189 nm and approximately 200 nm,
   wherein the frequency mixing module further comprises an optical cavity configured to recirculate an unconsumed portion of the pump frequency.

2. The laser of claim 1, wherein the fifth harmonic generator comprises a first stage configured to generate a second harmonic from a portion of the fundamental frequency.

3. The laser of claim 2, wherein the first stage includes a Lithium triborate (LBO) crystal.

4. The laser of claim 2, wherein the fifth harmonic generator further comprises:

a second stage configured to generate a fourth harmonic from the second harmonic; and
a third stage configured to generate the fifth harmonic by combining the fourth harmonic and a portion of the fundamental frequency.

5. The laser of claim 4, wherein at least one of the second and third stages includes at least one of an annealed Cesium Lithium Borate (CLBO) crystal, an annealed LBO crystal, a hydrogen-annealed CLBO crystal and a hydrogen-annealed LBO crystal.

6. The laser of claim 2, wherein the fifth harmonic generator further comprises:
   a second stage configured to generate a third harmonic by combining a portion of the second harmonic and a portion of the fundamental frequency; and
   a third stage configured to generate the fifth harmonic by combining the third harmonic and a portion of the second harmonic.

7. The laser of claim 6, wherein the second stage includes an LBO crystal or an annealed LBO crystal.

8. The laser of claim 6, wherein the third stage includes at least one of a Cesium Lithium Borate (CLBO) crystal, an annealed CLBO crystal, and a hydrogen-annealed CLBO crystal.

9. The laser of claim 1, wherein the fundamental laser comprises one of a Raman shifter, a Raman oscillator, and a Raman amplifier.

10. The laser of claim 9, wherein the Raman shifter, Raman oscillator or Raman amplifier includes one of a doped fused-silica optical fiber, a germania-doped fused-silica optical fiber, and an undoped fused-silica optical fiber.

11. The laser of claim 1, wherein the pump laser includes one of an ytterbium (Yb)-doped fiber and an infra-red diode laser.

12. The laser of claim 11, wherein the laser diode uses quantum dot technology.

13. The laser of claim 1, wherein the frequency mixing module includes an annealed Cesium Lithium Borate (CLBO) crystal or a hydrogen-annealed CLBO crystal.

14. A method of generating light, the method comprising:
    generating a pump frequency having a corresponding wavelength of between approximately 1105 nm and approximately 1130 nm;
    generating a fundamental frequency from a portion of the pump frequency, the fundamental frequency corresponding to a wavelength between approximately 1150 nm and approximately 1175 nm;
    generating a fifth harmonic from the fundamental frequency; and
    combining the pump frequency and the fifth harmonic to generate an output wavelength between approximately 189 nm and approximately 200 nm,
    wherein said combining the pump frequency and the fifth harmonic frequency includes recirculating an unconsumed portion of the pump frequency.

15. The method of claim 14, wherein said generating the fundamental frequency includes Raman shifting the pump frequency.

16. The method of claim 14, wherein said combining the pump frequency and the fifth harmonic frequency uses an annealed CLBO crystal or a hydrogen-annealed CLBO crystal.

17. The method of claim 14, wherein said generating the fifth harmonic frequency from the fundamental frequency comprises:
    generating a second harmonic from a portion of the fundamental frequency;

generating a fourth harmonic from the second harmonic; and generating the fifth harmonic by combining the fourth harmonic and a portion of the fundamental frequency.

18. The method of claim 14, wherein said generating the fifth harmonic frequency from the fundamental frequency comprises:

generating a second harmonic from a portion of the fundamental frequency;

generating a third harmonic by combining a portion of the second harmonic and a portion of the fundamental frequency; and generating the fifth harmonic by combining the third harmonic and a portion of the second harmonic.

* * * * *